(12) United States Patent  (10) Patent No.: US 8,574,280 B2
Yu et al.  (45) Date of Patent: Nov. 5, 2013

(54) SYSTEMS AND METHODS FOR ELICITING CUTANEOUS SENSATIONS BY ELECTROMAGNETIC RADIATION

(71) Applicant: Pine Development Corporation, Mountain View, CA (US)

(72) Inventors: William J. Yu, Mountain View, CA (US); Alexander A. Brownell, Bountiful, UT (US)

(73) Assignee: Pine Development Corporation, Mountain View, CA (US)

( * ) Notice: Subject to any disclaimer, the term of this patent is extended or adjusted under 35 U.S.C. 154(b) by 0 days.

(21) Appl. No.: 13/722,844

(22) Filed: Dec. 20, 2012

(65) Prior Publication Data

US 2013/0172965 A1 Jul. 4, 2013

Related U.S. Application Data

(60) Provisional application No. 61/579,776, filed on Dec. 23, 2011, provisional application No. 61/585,741, filed on Jan. 12, 2012.

(51) Int. Cl.
*G06F 3/041* (2006.01)
*A61B 5/06* (2006.01)

(52) U.S. Cl.
USPC ............................................. 607/89; 345/173

(58) Field of Classification Search
CPC ....................................................... G06F 3/016
USPC ................................. 607/88, 89, 100; 434/113
See application file for complete search history.

(56) References Cited

U.S. PATENT DOCUMENTS

| | | | |
|---|---|---|---|
| 6,038,595 A * | 3/2000 | Ortony | 709/218 |
| 6,921,413 B2 | 7/2005 | Mahadevan-Jansen et al. | |
| 7,488,341 B2 | 2/2009 | Merfeld | |
| 7,736,382 B2 | 6/2010 | Webb et al. | |
| 7,833,257 B2 | 11/2010 | Walsh, Jr. et al. | |
| 7,883,535 B2 | 2/2011 | Cantin et al. | |
| 7,883,536 B1 | 2/2011 | Bendett et al. | |
| 7,951,181 B2 | 5/2011 | Mahadevan-Jansen et al. | |
| 7,988,688 B2 | 8/2011 | Webb et al. | |
| 7,994,468 B2 * | 8/2011 | Duijve et al. | 250/221 |
| 8,012,189 B1 | 9/2011 | Webb et al. | |
| 8,160,696 B2 | 4/2012 | Bendett et al. | |

(Continued)

OTHER PUBLICATIONS

Himmer et al. ("Micromachined silicon nitride deformable mirrors for focus control," Opt. Lett. 26, 1280-1282 (2001).*

(Continued)

*Primary Examiner* — Sam Yao
*Assistant Examiner* — Nathan J Jenness
(74) *Attorney, Agent, or Firm* — Jared L. Cherry; Phillips Ryther & Winchester

(57) ABSTRACT

The present disclosure provides various systems and methods for inducing cutaneous sensations by delivering electromagnetic radiation to directly or indirectly excite neural tissue. An electromagnetic radiation source, such as one or more infrared lasers, may be used to transcutaneously excite neural tissue. The excited neural tissue may be interpreted by the user's nervous system as cutaneous sensations. Accordingly, a system as described herein may be used to induce sensations to allow actual cutaneous sensations to be simulated. A system for inducing a cutaneous sensation via transcutaneously focused electromagnetic radiation may be incorporated in a display to provide cutaneous sensation feedback or used as a separate accessory component associated with a display. Numerous additional applications and variations are provided herein.

18 Claims, 18 Drawing Sheets

(56) References Cited

U.S. PATENT DOCUMENTS

| | | | |
|---|---|---|---|
| 8,330,729 | B2 | 12/2012 | Tachi et al. |
| 8,456,448 | B2 * | 6/2013 | Rekimoto ............ 345/175 |
| 2002/0002391 | A1 | 1/2002 | Gerdes |
| 2006/0154216 | A1 * | 7/2006 | Hafez et al. ............ 434/113 |
| 2007/0060984 | A1 | 3/2007 | Webb et al. |
| 2007/0285402 | A1 * | 12/2007 | Lim et al. ............ 345/173 |
| 2008/0077200 | A1 | 3/2008 | Bendett et al. |
| 2009/0069871 | A1 | 3/2009 | Mahadevan-Jansen et al. |
| 2010/0262212 | A1 | 10/2010 | Shoham et al. |
| 2010/0292758 | A1 | 11/2010 | Lee et al. |
| 2012/0068952 | A1 * | 3/2012 | Slaby et al. ............ 345/173 |
| 2012/0179228 | A1 | 7/2012 | DeCharms |

OTHER PUBLICATIONS

Shao et al. ("3-D MOEMS mirror for laser beam pointing and focus control," Selected Topics in Quantum Electronics, IEEE Journal of, vol. 10, No. 3, pp. 528,535, May-Jun. 2004).*

Cayce, Infrared Neural Stimulation of Thalamocortical Brain Slices, IEEE Journal of Selected Topics in Quantum Electronics, vol. 16, No. 3, May/Jun. 2010, 8pgs.

Dummer, Development of VCSELs for Optical Nerve Stimulation, 7pgs.

Industrynews, Eurotimes, vol. 16, Issue 6, p. 44, 1pg.

Dittami, Intracellular calcium transients evoked by pulsed infrared radiation in neonatal cardiomyocytes, Journal of Physiology 589.6 (2011) pp. 1295-1306, 12 pgs.

Jindra, Epidermal laser stimulation of action potential in the frog sciatic nerve, Journal of Biomedical Optics 15(1), 015002-1-15002-6, Jan./Feb. 2010, 6pgs.

Kajimoto, Tactile Feeling Display using Functional Electrical Stimulation, Graduate School of Engineering, The University of Tokyo, ICAT 1999, Tokyo, Japan, 8pgs.

Lee, Virtual Surface Characteristics of a Tactile Display Using Magneto-Rheological Fluids, Open Access, Sensors 2011, ISSN 1424-8220, 12pgs.

L'Etang, The effect of Laser Wavelength in the Simulation of Laser Generated Surface Waves in Human Skin Model, Proceedings of the 28th IEEE, EMBS Annual International conference, NY, USA, Aug. 30-Sep. 3, 2006, 4pgs.

Rajguru, Infrared photostimulation of the crista ampullaris, Journal of Physiology 589.6 (2011) pp. 1283-1294, 12pgs.

Richter, Neural stimulation with optical radiation, Laser & Photonics Reviews 5, No. 1, 60-80, 2011, 13pgs.

Stockbridge, Focusing through dynamic scattering media, Optics Express 15087, vol. 20, No. 14, Jul. 2, 2012, 7 pgs.

Vellekoop, Phase control algorithms for focusing light through turbid media, Optics Communications 281 3071-3080, 2008, 10pgs.

Vellekoop, Focusing light through living tissue, Optical Coherence Tomorgraphy and Coherence Domain Optical Methods in Biomedicine XIV, 2010, 10pgs.

Sui, Visual Prosthesis for Optic Nerve Stimulation.

Wells, Application of infrared light for in vivo neural stimulation, Journal of Biomedical Optics 10(6), 064003-1-064003-12, Nov./Dec. 2005, 12pgs.

Wells, Optical Stimulation of neural tissue in vivo, Optics Letters, vol. 30, No. 5, p. 504-506, Mar. 1, 2005, 3pgs.

Wells, Optically Mediated Nerve Stimulation: Identification of Injury Thresholds, Wiley InterScience, Lasers in Surgery and Medicine 39:513-526, Jul. 23, 2007, 14pgs.

* cited by examiner

SYSTEMS AND METHODS FOR ELICITING CUTANEOUS SENSATIONS BY ELECTROMAGNETIC RADIATION

RELATED APPLICATIONS

The present application claims the benefit under 35 U.S.C. §119(e) of U.S. Provisional Patent Application No. 61/579,776, filed Dec. 23, 2011 titled "SYSTEMS AND METHODS FOR OPTICALLY EXCITING NEURAL TISSUE FOR HAPTICS APPLICATIONS" and Provisional Patent Application No. 61/585,741, filed Jan. 12, 2012 titled "SYSTEMS AND METHODS FOR OPTICALLY EXCITING NEURAL TISSUE FOR HAPTICS APPLICATIONS," both of which are incorporated herein by reference in their entireties.

TECHNICAL FIELD

The present disclosure is directed to systems and methods for directly or indirectly exciting neural tissue using electromagnetic radiation. More particularly, the present disclosure is related to stimulation of neural or other excitable tissues using electromagnetic radiation for inducing cutaneous sensations.

BRIEF SUMMARY

According to various embodiments, a system for inducing cutaneous sensations, may comprise an electromagnetic radiation emission system configured to emit electromagnetic radiation suitable for directly or indirectly exciting neural tissue. The system may also include an electronic display configured to display a graphical user interface and a detection system configured to detect a point of contact (such as a finger contact) with the display. A controller configured to transmit a control signal to the electromagnetic radiation emission system to cause the electromagnetic radiation emission system to direct electromagnetic radiation at the contact detected by the detection system to directly or indirectly excite neural tissue associated with the contact in order to induce a cutaneous sensation. According to some embodiments, the electromagnetic radiation emission system may further comprise at least one focusing element controllable for selectively focusing the electromagnetic radiation emitted by the electromagnetic radiation emission system. Transcutaneously focused electromagnetic radiation may include single or multiple beams of electromagnetic radiation coincident at a focal point. Alternatively, a splitting element may be utilized in some embodiments in order to direct electromagnetic radiation from one source of electromagnetic radiation to a plurality of points of contact. Another embodiment would be a single source of electromagnetic radiation emission that is redirected or switched by the controller to individual fiber optic lines (e.g. an optical switch), which are spatially arranged to allow for specific illumination/irradiation at specific points on the user. Finally, some embodiments may incorporate multiple sources of electromagnetic radiation that may be selectively directed toward multiple points of contact.

The system may further comprise a storage medium containing a library of cutaneous sensations, each of which may be defined by a set of characteristics of the electromagnetic radiation. The controller may be configured to modulate the characteristics of the electronic radiation emitted by the electromagnetic radiation emission system to induce a specific cutaneous sensation. These individual or pre-defined sensations can also be combined and tailored via the controller to create unique cutaneous sensations.

At least one of the cutaneous sensations may be defined by a set of characteristics of the electromagnetic radiation in at least two locations in the neural tissue separated by more than a two-point discrimination region. The controller may be configured to modify or modulate one or more characteristics of the electromagnetic radiation emitted by the electromagnetic radiation emission system to induce a cutaneous sensation corresponding to an object displayed on the graphical user interface at the location of the contact with the electronic display. According to some embodiments, the characteristics of the electromagnetic radiation modified or modulated by the controller may include pulse width, pulse repetition rate, shape, amplitude, fluence, depth, frequency, location(s), spot size, wave shape, duty cycle, rasterization patterns, and the like.

The electromagnetic radiation emission system may comprise Light-Emitted Diodes (LEDs) or various forms of laser sources, including edge-emitting and surface emitting semiconductor lasers for example, and nonlinear frequency conversion of these laser sources. Of course, according to various embodiments, other types of visible and electromagnetic radiation sources may also be utilized.

The electronic display may be a touch screen electronic display, and the detection system may utilize a touch screen digitizer or the like of the touch screen electronic display to detect the contact and determine the point of contact or area of contact with the user. The electromagnetic radiation emission system may be part of a moveable stage configured to move relative to the plane of the electronic display, and the controller may be configured to control the movement of the stage to direct the electromagnetic radiation to the contact detected by the detection system. The stage may comprise at least one magnet, and the controller may be configured to control the movement of the stage relative to the plane of the electronic display using a series of electromagnets proximate at least two edges of the electronic display. Alternatively, other forms of mechanical actuation may be utilized to reposition the moveable stage. The moveable stage will allow for mounting one of a mirror(s) and a focusing element(s) such as a lens that can direct the incoming electromagnetic radiation from the perimeter of the display to perpendicular to the plane of the display and into the point of user contact.

Alternatively, the electromagnetic radiation emission system may be configured to direct the electromagnetic radiation to the point of contact detected by the detection system via the stage via fiber optic cable mounted to a moveable stage. The controller may be configured to cause the electromagnetic radiation emission system to transcutaneously focus electromagnetic radiation at the contact using a procession pattern bounded by a two-point discrimination region.

The system may further comprise a sub-threshold electrical stimulation system configured to electrically stimulate a portion of the user. According to some embodiments, the electrical stimulation system is used to elicit electrical stimulation to achieve a subthreshold value that can later use electromagnetic radiation to achieve threshold and achieve sensation. The controller may be further configured to adjust the fluence of the electromagnetic radiation based on calibration results. For example, the calibration results may define a minimum energy density to induce a cutaneous sensation in the contact. The calibration results may be obtained from a calibration phase, performed by directing electromagnetic radiation of various fluences at the point of contact, receiving feedback from a user indicating which of the electromagnetic radiation pulses induced a cutaneous sensation in the contact;

and associating a minimum energy density to induce a cutaneous sensation with the lowest fluence indicated by the user as having induced a cutaneous sensation.

The system may further comprise a thermal feedback system configured to measure a temperature associated with the contact, and the controller may be configured to dynamically control the electromagnetic radiation emission system to only deliver the appropriate fluence to achieve the desired stimulation. According to one embodiment the temperature of the finger or other body part is determined by a thermistor, or the like, to provide the control system with an indication of the skin temperature. According to another embodiment, the temperature of the glass is maintained at a certain known temperature using feedback from an embedded thermistor, or the like, to provide an indication of the glass temperature.

The thermal feedback system may comprise a non-contact infrared thermometer, a thermistor, and/or a thermocouple.

The system for inducing cutaneous sensations may be implemented on a user interface component instead of or in addition to a display. A discrete user interface component may be associated with a display in some embodiments. The user interface component may comprise a track pad or a keyboard or a mouse key or any portion thereof. According to some embodiments the user interface component may comprise an enclosure, and the enclosure may be configured to receive at least one finger (or other portion of the user, such as a hand) within the enclosure. The enclosure may comprise a glove configured to enclose two or more fingers, a finger wrap configured to receive a single finger, or a hand enclosure configured to receive a hand. According to one embodiment, a finger wrap or finger sleeve may include embedded fiber optic lines. An optical switch may be used to deliver electromagnetic radiation to a target area. Further, such embodiments may be configured to deliver a rasterized pattern of electromagnetic energy in order to stimulate multiple target areas.

The user interface component may be associated with a display, and the controller may be configured to modify one or more characteristics of the electromagnetic radiation emitted by the electromagnetic radiation emission system to induce a cutaneous sensation corresponding to an object displayed on the display. The system may be integrated into a peripheral computing device configured to allow a user to provide input to a computing device, and the user interface component may comprise a surface of the peripheral device. The peripheral computing device may comprise one of a computer mouse and a computer keyboard, and the user interface component comprises a surface of a button.

In one embodiment, a system for communicating visual information via cutaneous sensations may comprise an imaging device configured to image at least one object; an electromagnetic radiation emission system configured to emit electromagnetic radiation suitable for directly or indirectly exciting neural tissue. The system may further include an interface component configured to deliver electromagnetic radiation to a target area of a user's skin and a controller configured to control operation of the electromagnetic radiation emission system. The controller may map at least one object imaged by the imaging device to a cutaneous sensation and transmit a control signal to the electromagnetic radiation emission system to cause the electromagnetic radiation emission system to deliver electromagnetic radiation at the point of contact to directly or indirectly excite neural tissue and thereby induce a cutaneous sensation at the point of contact.

In another embodiment, a multi-layer display configured to induce cutaneous sensations may comprise a touch screen digitizer layer or the like configured to detect a point of contact with a user. The multi-layer display may also include an electronic display layer configured to display objects; a spatial light modulator (SLM) layer configured to dynamically focus and steer electromagnetic radiation; a VCSEL and lenslet array layer configured to selectively emit electromagnetic radiation suitable for exciting neural tissue. A controller may be configured to control the SLM layer and the VCSEL and lenslet array layer to deliver electromagnetic radiation at the point of contact to thereby directly or indirectly excite neural tissue to induce a cutaneous sensation at the point of contact.

A method for inducing cutaneous sensations may comprise displaying graphical information on an electronic display; detecting a point of contact with a user on the display; and transcutaneously focusing and steering electromagnetic radiation at the contact of the finger to excite neural tissue in the finger to induce a cutaneous sensation.

Various methods are also disclosed herein for inducing cutaneous sensations. Such methods may include displaying a graphical user interface on an electronic display and detecting a point of contact of a finger on a haptic feedback surface associated with the electronic display. Further the method may include generating a control signal to cause an electromagnetic radiation emission system to deliver electromagnetic radiation. In response to the control signal, electromagnetic radiation may be delivered at the point of contact to directly or indirectly excite neural tissue in the finger and thereby induce a cutaneous sensation.

BRIEF DESCRIPTION OF THE DRAWINGS

Non-limiting and non-exhaustive embodiments of the disclosure are described herein, including various embodiments of the disclosure illustrated in the figures listed below.

Figure 1:
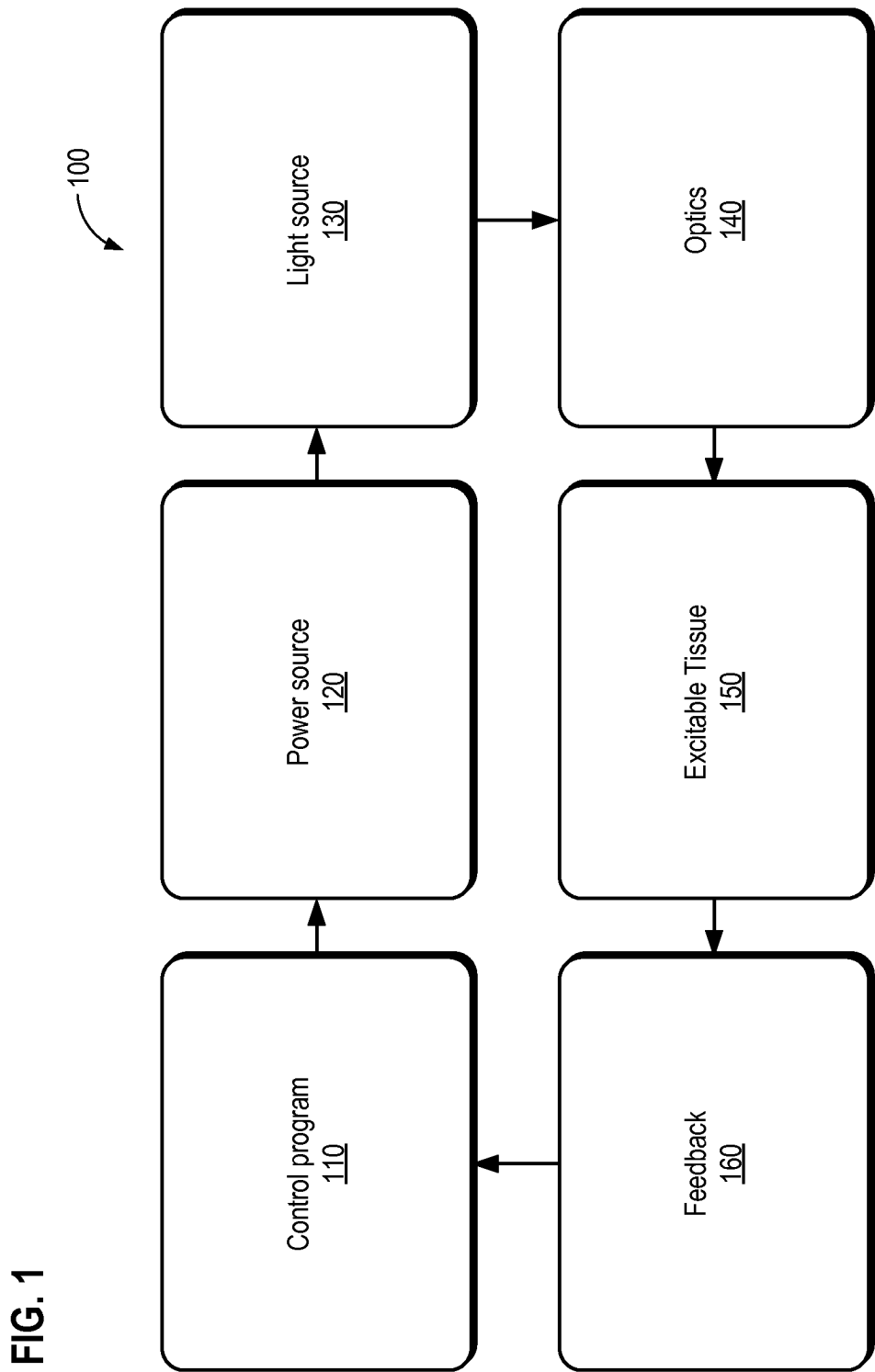
FIG. 1 illustrates a block diagram of a system for exciting tissue using electromagnetic radiation, according to certain embodiments.

In the following description, numerous specific details are provided for a thorough understanding of the various embodiments disclosed herein. The systems and methods disclosed herein can be practiced without one or more of the specific details, or with other methods, components, materials, etc. In addition, in some cases, well-known structures, materials, or operations may not be shown or described in detail in order to avoid obscuring aspects of the disclosure. Furthermore, the described features, structures, or characteristics may be combined in any suitable manner in one or more alternative embodiments.

DETAILED DESCRIPTION

According to various embodiments, electromagnetic radiation may be used to induce apparent cutaneous sensations in a user. Accordingly, the various embodiments of the systems described herein are configured to induce cutaneous sensations through the application of transcutaneous electromagnetic radiation. In some embodiments, mechanical deformation of the skin is used to produce tactile sensation. Challenges associated with using mechanical devices for creating haptic sensations may include the inertia of moving parts and the difficulty in miniaturization to create sufficiently high resolution. In other embodiments, direct electrical stimulation of tissue may be used. However, electrical stimulation often has poor spatial resolution due to current spreading between electrodes.

Electromagnetic radiation, such as light emitted in the infrared or visible spectrum, may be applied to a user's skin in order to stimulate neural tissue in the skin and thereby induce action potentials, either directly or indirectly, at the site of irradiation. Irradiation of the skin that induces, either directly or indirectly, action potentials in the peripheral nervous system which are highly spatially selective, and may thus achieve high resolution and may be utilized in connection with many applications.

Lasers may be used in ablative and non-ablative applications. Ablative laser systems may impart sufficient energy to the tissue so that some portion of the tissue architecture may be destroyed or otherwise transformed. For example, ablative lasers may be used in surgery to replace or supplement the use of scalpels and cautery instruments. Ablative lasers may also be used in aesthetic dermatology to encourage dermal remodeling. At somewhat lower energies, both ablative and non-ablative, systems may be adapted for port wine stain removal using photocoagulation techniques that selectively destroy the excessive accumulation of blood vessels. Non-ablative laser technologies may apply lower energies or fluences than ablative lasers. Non-ablative lasers may be used to promote wound healing, relax sore muscles, and potentially alter cellular function in various ways. Low-level light therapy (LLLT) devices have applications in medical and veterinary uses, as well as in the field of dentistry. According to various embodiments described herein, electromagnetic radiation may be used at wavelengths at energies that do not cause tissue damage. According to some embodiments, the energy density utilized by some embodiments may be higher than that of traditional LLLT devices.

Electromagnetic radiation suitable for exciting neural tissue, either directly or indirectly, may include specific wavelengths or a range of wavelengths, according to various embodiments. The application of electromagnetic radiation to nervous tissue may elicit action potentials. The system may utilize a wide range of one or more different wavelengths between approximately 400 nanometers (nm) and 8000 nm, including but not limited to 650, 808, 850, 860, 885, 915, 940, 980, 1064, 1120, 1310, 1450, 1470, 1490, 1495, 1540, 1550, 1850, 1862, 1870, 2000, 2100, 2120, 3000, 4000, and 6000 nm. The present disclosure contemplates several different embodiments of the device with different electromagnetic radiation sources. For example, one embodiment uses a laser as the electromagnetic radiation source. In another embodiment, the electromagnetic radiation source may utilize one or more LEDs. In another embodiment, a flash tube broad-spectrum light source may be utilized. Any of a wide variety of electromagnetic radiation sources capable of delivering electromagnetic radiation at a sufficient power density may be utilized. Some embodiments may utilize a single wavelength source, filter all but a single wavelength of a broad-spectrum source, and/or utilize a multi-wavelength source of electromagnetic radiation. In some embodiments, a filter may be placed at any point between the electromagnetic radiation source and the tissue to be stimulated.

The present disclosure provides various embodiments of systems and methods for inducing cutaneous sensations using transcutaneously delivered electromagnetic radiation. As used herein, the terms electromagnetic radiation represents the breadth of the electromagnetic spectrum, as applicable to the present disclosure. In various embodiments, tissue may be transcutaneously irradiated for the purpose of simulating the sensations of cutaneous touch. The cutaneous sensations may represent physical traits of actual objects at a remote location, or can represent simulated objects.

For example, a system for inducing cutaneous sensations using transcutaneously delivered electromagnetic radiation may be used for any number of tactile applications, such as, but not limited to, telepresence medicine, compact electronic Braille displays, virtual product online shopping, representing virtual and physical objects and drawings in computer generated images and computer aided drafting (CAD), for touch screen feedback, control feedback, and/or entertainment and gaming devices. The use of electromagnetic radiation for stimulating neural tissue may be more responsive than a mechanical system and may provide higher spatial resolution than a purely electrical system. In addition, the lack of moving parts may result in higher reliability and lower maintenance of the system.

In some embodiments, transcutaneously delivered electromagnetic radiation may be used to induce cutaneous or subcutaneous sensations for use in less-than-lethal weapons. Less-than-lethal weaponry is widely used by military and police forces for crowd control and other situations where slowing or immobilizing a person is preferable to causing serious injury or death. Transcutaneous application of electromagnetic radiation may be used to cause a sensation on or beneath the skin. For example, a less-than-lethal weapon utilizing transcutaneously applied electromagnetic radiation may be used to cause sensations associated with burning, pressure, scraping, cutting, and/or other unpleasant or painful sensations that may deter a person from a particular course of conduct. Such a system may be configured to cause no damage, or minimal damage, to tissue. Rather, the system may simply induce sensations in the brain as being extremely unpleasant or injurious.

In some embodiments, a patch or plate, which is adhered to the skin, may be used to transmit electromagnetic radiation to/through the skin. Such a device may be adapted to communicate tactile information to the wearer discretely and/or silently. Such a system may be used in silent military applications.

In some embodiments, a system configured to induce cutaneous sensations via transcutaneously focused electromagnetic radiation may be used to induce pleasant sensations as well. For example, a system may be adapted to comfort and/or calm premature infants in incubators. The system may simulate human contact without exposing them to the contamination that the incubator intends to avoid. In some embodiments such a patch could provide comfort to older patients as well. Those afflicted with depression, seasonal affective disorder, or other mental illness that have shown response to vagal nerve stimulation. Cutaneous stimulation on the proper body parts may also help alleviate some of their symptoms. Also, in autism and other developmental disorders many individuals engage in autostimulation behaviors. In some of these cases the autostimulation behavior can cause serious injury. Optical stimulation of these patients may prove to satisfy the desire for stimulation in a less injurious manner.

A system may utilize a control program to control the application of electromagnetic radiation. For example, the electromagnetic radiation may be directed to the tissue in such a way that only a small portion of the tissue is irradiated. The tissue may be excited in such a way that the brain perceives it as mechanical stimulation. The amount of energy imparted to the tissue may be the minimum necessary to reliably and reproducibly elicit the desired response. In some embodiments, the control program may be calibrated for a set of users and/or a specific user. In some embodiments, a feedback mechanism may be used to dynamically adjust the output. For example, the control program may be initially calibrated and then dynamically adjust the amplitude, focus, rasterization pattern, and/or other attributes of the electromagnetic radiation based on a thermal sensor to protect the skin from damage.

The control program may utilize an infrared imaging device or other temperature probe to detect the surface temperature of the skin and make appropriate adjustment to the stimulation protocol. In another embodiment the feedback may be quasi-closed loop and may be accomplished by incorporating calculations from a proprietary computer simulation, and/or empirical data collected from various human or phantom tissue testing in the form of a look-up table where the stimuli delivered are known to change the tissue temperatures and subsequent stimuli are adjusted accordingly.

Tactile and/or other cutaneous sensations may be created by the activation of mechanoreceptors that are normally triggered. These receptors are distributed unequally in different areas of the skin. In order to selectively stimulate a different number of receptors, neuronal axons, or other excitable tissues the application of optical energy may be applied in a controlled manner.

In some embodiments, a plurality of optical focusing devices may be used to direct electromagnetic radiation to the tissue. This may be accomplished through the use of any combination of lenses, mirrors, fiber optics, and/or other electromagnetic manipulation materials. The incident electromagnetic radiation may be focused to provide a spot size, large enough to assure stimulation of excitable tissues, while remaining small enough that collateral heating of non-excitable tissues are minimized. The beam shape of the electromagnetic radiation may be controlled to limit collateral heating of non-excitable tissues. For example, a highly converging beam with short focal region may be focused at or beneath the skin surface. In other embodiments, the electromagnetic radiation may comprise several beams of electromagnetic radiation focused transcutaneously. Focusing electromagnetic radiation may include the utilization of optical components such as lenses and/or mirrors, and/or the usage of coincident beams of electromagnetic radiation. The focal point(s) may be at a location(s) within the tissue where electromagnetic radiation can be used to produce neural excitation.

In some embodiments, to avoid overheating of a single area of tissue, beam procession may be used within a small area. The procession of the beam may be confined to an area where different stimuli are spatially indistinguishable by the brain. In other words, the area of confinement for the procession may be experienced by the user as stimulation of the same point on the skin. Accordingly, two-point discrimination may vary depending upon which area of a user's body is irradiated.

Accordingly, by rasterizing the applied beam of electromagnetic radiation, the system may stimulate many points on the skin simultaneously, or nearly simultaneously, and/or may reduce cutaneous and/or subcutaneous thermal buildup. In one embodiment, the beam is scanned or rastered through the use of a device, such as a galvanometer-based optical scanner. In another embodiment, one or more prisms may split the beam and the split beams may be shuttered, such as via a mechanical and/or liquid crystal display (LCD) based spatial light modulation system. In another embodiment, a Spatial Light Modulator (SLM) may be used to dynamically modify the wavefront of the electromagnetic radiation in order to adaptively focus the beam inside the skin layer. A grating structure can also be written on the same SLM in order to scan the electromagnetic radiation over the skin.

In another embodiment, the beam may be split and transmitted via a multi-bundle fiber array combined with shutter control at the output of each of the fibers from the bundle. In one embodiment, optical rastering can be implemented by the use of a fiber bundle with N fibers and a 1×N optical switch. The stimulation light can come from either a single LED/laser source, or it can be the combined output from M LED/laser sources. By connecting a 1×N optical switch to an N-fiber bundle, the light can be sequentially directed to any one of the N-fibers in the bundle by the use of the optical switch.

In another embodiment, digital light processing technology may be used to split and direct multiple beams. In one embodiment, a two-dimensional motion stage, described in terms of an X-Y coordinate system, may be used to move the electromagnetic radiation source. In some embodiments, a tilting mechanism may be used to adjust the incident angle and allow for a greater area for beam delivery. That is, the electromagnetic radiation source may be moved within a limited two-dimensional array combined with a tilting mechanism to widen the effective two-dimensional range of the system.

Any of the variously described embodiments of systems for inducing cutaneous sensations via transcutaneously focused electromagnetic radiation may be integrated within a display, such as a touch screen display. For example, a system may be integrated within an LCD or organic LED (OLED) screen. For example, a system may be integrated and associated with a pixel or cluster of pixels adjacent to an electromagnetic radiation source or electromagnetic radiation transmission element. The system may be configured to provide tactile feedback associated with the display or touchscreen display. In other embodiments, the electromagnetic radiation source and/or electromagnetic radiation transmission element(s) may be placed behind a display that is transparent to the electromagnetic radiation so that the electromagnetic radiation passes through the display or vias built into the display.

For example, the electromagnetic radiation may be directed through the surface of a touch screen display into the finger, fingers, and/or hand of a user to induce a cutaneous sensation. A system, according to any of the embodiments described herein, may be integrated into an interactive display such as on a smartphone, tablet computer, computer monitor, or television. In such devices, the location or placement of a finger or other object may be determined by hardware built directly into the screen and/or software. The location and contact area information may be utilized by the system to irradiate only when and where tissue (e.g., a finger) is present. In addition to location and contact area information, movement attributes such as speed and direction may be determined and used by the control system to dynamically adjust the electromagnetic radiation transmission settings. For example, the sensations induced by the transcutaneously focused electromagnetic radiation may simulate a textured surface. The textured surface felt may be dynamic and/or changeable. The sensations could also be used as feedback for actions performed, such as a button press. The stimulation surface may also be a track pad or other dedicated non-display surface through which the electromagnetic stimulating energy may pass.

In one embodiment, a system for inducing cutaneous sensations using transcutaneously focused electromagnetic radiation may be embodied as an off-display device associated with a second device. For example, a system may interact with a user's single finger, multiple fingers, or a full hand. In some embodiments, users may insert a portion of their bodies, such as a finger, hand, arm, etc. within the stimulating area of the device. The user, or portion of the user inserted within the system, could be held immobile or allowed to move. The system may induce sensations associated with virtual objects such that they feel or provide simulated sensations associated with corresponding physical objects. In some embodiments, the portion of the user to be irradiated with electromagnetic radiation may be decoupled from other surfaces, so as to limit sensations other than those induced via the transcutaneously focused electromagnetic radiation.

In some embodiments, the off-display embodiment may be passive in the sense that the tissue to be stimulated cannot move to interact with a display of the object being represented. In other embodiments, the off-display embodiment may be partially interactive by allowing the finger(s) and/or hand to move and/or respond within the off-display system. In such an embodiment, the system may track movement and make appropriate adjustments to the stimulating beams for appropriate focus.

In another embodiment, a covering or housing may be secured to a finger(s) or hand of a user that allows the user to interact with a display. The covering may prevent the finger(s) or hand from receiving mechanical stimulation, such as from the surface of the touch screen display. Electromagnetic radiation may be directed onto the finger pad(s) of the user via fiber optics and/or other lenses or mirrors within the covering. The fiber optics may be connected to a remote electromagnetic radiation source. The covering may allow for interaction with a display or other interface. The electromagnetic radiation may induce sensations during the interaction and the covering may limit extraneous sensations (such as the texture of the display). In some embodiments, the display may be a computer or phone screen. The display could also be a holographic or virtual reality display presented in two or three-dimensions.

A library of stimulation protocols may dictate the various sensations that can be induced by the system. Appropriately stimulating different receptors, axons, dendrites or other excitable tissues with electromagnetic radiation at the appropriate place on/within the skin and with the appropriate repetition rates may be used to effectively replicate tactile stimulation sensations experienced by touching a physical object. A library may contain the basic components of complex sensations that, when combined appropriately, are capable of inducing a wide range, or even all, of the cutaneous sensations, including, but not limited to, those involving textures, pain, hot, cold, wet, dry, sticky, etc. Thus, a controller may modify the characteristics of the electromagnetic radiation to change the pulse width, shape, amplitude, energy density, duty cycle, frequency, depth, location(s), spot size, wave shape, modulation characteristics, rasterization patterns and/or other characteristics of the electromagnetic radiation beam to induce any of a wide variety of cutaneous sensations. In some embodiments, these pre-defined cutaneous sensation effects can be combined and mixed appropriately to create new sensations within predetermined safety limits to prevent harm to the user.

The stimulation protocols may include waveforms of various shapes and patterns. The various pulses delivered are combined into trains consisting of, but not limited to, square, triangular, trapezoidal, and sinusoidal shaped pulses. Electromagnetic radiation may be continuously emitted, pulsed, electronically shuttered, pulse-width modulated (PWM), and/or otherwise modulated or pulsed. The spot size of the incident electromagnetic radiation may also be varied to create different sensory effects. This spot could be dynamically altered by movable lenses and/or by a variable aperture.

Obtaining tactile information may be done by a number of different means. In one embodiment, a system may be configured to obtain tactile information for replication using an ultrasonic probe. An ultrasonic probe may be used to gather topographical information of an object, how compliant an object is, and/or subsurface characteristics of an object. In some embodiments, a laser may be used to determine the characteristics of a surface of an object. In some embodiments, a 3-D camera system may also be used to capture surface characteristics of an object. In another embodiment, a series of probes mounted on calibrated springs may be utilized to mechanically determine characteristics of a surface. As the spring is compressed, its displacement gives the appropriate information about the object's properties. Additionally, a differential transformer may be used to measure linear or translational displacements on a surface.

In one embodiment, a system, as described herein, may be utilized by the user to measure physical characteristics of objects and induce corresponding sensations for the user. For example, an imaging device may be used to scan the surface of an object. The system may translate the image into a series of tactile sensations to be induced using transcutaneously focused electromagnetic radiation. In some embodiments, characteristics such as color, grey scale, line thickness, temperature, and the like, may be translated into tactile sensations.

In one embodiment, a sub-threshold electrical stimulation system may be combined with transcutaneously focused electromagnetic radiation. For example, electrodes may be placed near or at the location of the user where electromagnetic radiation is to be received. The electrodes may be configured to provide sub-threshold stimuli in the general area. Accordingly, the electrodes themselves may not produce any action potential in the mechanoreceptors or their afferent axons. The electrical stimuli may be cyclic at high rates corresponding to the necessary electromagnetic stimulation. Electromagnetic radiation may be applied in conjunction with the cyclical electrical stimuli. According to such an embodiment, since the electrical stimuli provides a sub-threshold stimulation, the electromagnetic radiation may be used to induce cutaneous sensations at lower energy densities and may also provide for greater selectivity of action potentials from Aβ and Aδ neural fibers that convey tactile information over C fibers that carry pain and thermal information.

In one embodiment, the tactile information conveyed by a system as described herein may be associated with a tactile logo or tactile signature. A static or dynamic sensation may be incorporated into any number of applications. For example, a tactile logo may be felt beneath a visually displayed web page. The logo may not be visually displayed and only felt by the user. Such functionality could be incorporated in both on-display and off-display systems as described herein.

For example, the tactile logo could be generated constantly beneath the finger every time the finger is in contact with the screen. Alternatively, the tactile logo may be associated with specific displayed content, such as, but not limited to, a text, images, and/or animation delivered to the user, such that when a specific object or text is touched by the user, the logo is felt. A recognizable tactile logo could let the user know who is sponsoring a certain web page, that a page is secure, or in another application without taking up visual space on the screen. This may be particularly valuable on a mobile phone or other device with limited screen space. Customers could purchase tactile logos for inclusion on personal or company web pages, applications, and/or the like.

Tactical representations may be encoded similar to black and white digital photographs. For example, a tactical representation may be represented by x and y coordinates with amplitude or depth information encoded at each point. Each point may be called a tixel (tactile image element). The number of tixels and the range of possible representations (e.g., bits) for amplitude or depth information may define the resolution of a tactile representation. Each surface of an object may be represented by a tactile image or code. With a library of such images the surfaces of these objects may be represented as a corresponding induced sensation to the user. In another embodiment, thermal images that show temperature fields or gradients can be represented as tixels and representations (e.g., bits) for temperature or temperature gradients may define the resolution of a tactile thermal representation.

In many embodiments, the user interface may be a flat surface on top of which cutaneous sensations are created. In such embodiments, the surface textural information and an object's shape and compliance may be conveyed to the user. In another embodiment, an object's temperature and temperature gradient information may be conveyed to the user. In embodiments in which a user's hand, finger, or other portions of the body are free to move in three dimensions, the surface information of a three-dimensional object may be conveyed.

A library of cutaneous tactile sensations and effects may be collected and stored in a control program or a separate memory location. Additionally, custom or combinations of sensations may be created. Sensations can be derived from a combination of pre-formed sensations dynamically calculated in software or stored for subsequent retrieval and use. Sensations may be based on empirical data, based on physiological testing, algorithmic data, and/or derived from initial calibration data. In one embodiment, algorithms used to determine sensations may account for variables, including but not limited to reflectance, temperature, finger speed, finger pressure, and tixel data to appropriately deliver the desired sensation(s).

In various embodiments, a controller or control system may be implemented as any combination of hardware, firmware, and/or software. For example, a controller may be implemented as a field-programmable gate array (FPGA). In some embodiments, an electronic controller may be distinct from other components of the system for inducing sensations using transcutaneously focused electromagnetic radiation. The system may include microprocessors and other electronic components associated with displays, touch screens, data storage, data connectivity, memory, non-transitory computer readable media, etc.

Some of the infrastructure that can be used with embodiments disclosed herein is already available, such as general-purpose computers, computer programming tools and techniques, digital storage media, and communication networks. A computing device or other electronic controller may include a processor, such as a microprocessor, a microcontroller, logic circuitry, and/or the like. The processor may include a special-purpose processing device such as application-specific integrated circuits (ASIC), programmable array logic (PAL), programmable logic array (PLA), a programmable logic device (PLD), FPGA, or another customizable and/or programmable device. The computing device may also include a machine-readable storage device, such as non-volatile memory, static RAM, dynamic RAM, ROM, CD-ROM, disk, tape, magnetic storage, optical storage, flash memory, or another machine-readable storage medium. Various aspects of certain embodiments may be implemented using hardware, software, firmware, or a combination thereof.

The embodiments of the disclosure may be understood with reference to the drawings, wherein like parts are designated by like numerals throughout. The components of the disclosed embodiments, as generally described and illustrated, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments.

FIG. 1 illustrates a block diagram of a system 100 for exciting tissue using electromagnetic radiation from a light source 130, according to one embodiment. According to various embodiments, a system 100 may include a control program, 110, a power source 120, a light source 130, one or more optical components 140 for transcutaneously focusing electromagnetic radiation from the light source 130 on excitable tissue 150, and a feedback system 160.

As illustrated, the light source 130, or other electromagnetic radiation source, may generate pulses of light at appropriate energies and duration to stimulate excitable tissues, mechanoreceptors, and/or innervating afferent axons. According to various embodiments, the pulse duration of the light source 130 may be in the range from 1 μs to 500 ms and stimulation frequency may be in the range from 0 Hz to 1000 Hz. Other pulse ranges and/or frequency ranges capable of stimulating excitable tissues may be utilized. In some embodiments, one or more optical components 140 may be used to focus the light on or within the excitable tissue 150. The optical components 140, in conjunction with the light source 130, may be configured to minimize radiation exposure of non-excitable tissue and/or avoid excessive heating of the excitable tissue 150. Light emitted by the light source 130 may, directly or indirectly, excite action potentials to induce sensations corresponding to tactile sensations, as interpreted by the central nervous system.

The feedback system 160 may measure skin temperature, pressure from the user on the system, user movement relative to the system, and/or to determine effectiveness of various incident energies and points of stimulation. The feedback system may provide information to the control program for dynamically adjusting the inducement of cutaneous sensations via the transcutaneously focused electromagnetic radiation emitted by the light source 130. The control program 110 may be implemented in hardware, firmware, and/or software. The control program may communicate with and/or control the feedback system 160, the optical components 140, the light source 130, and/or the power source 120.

Figure 2:
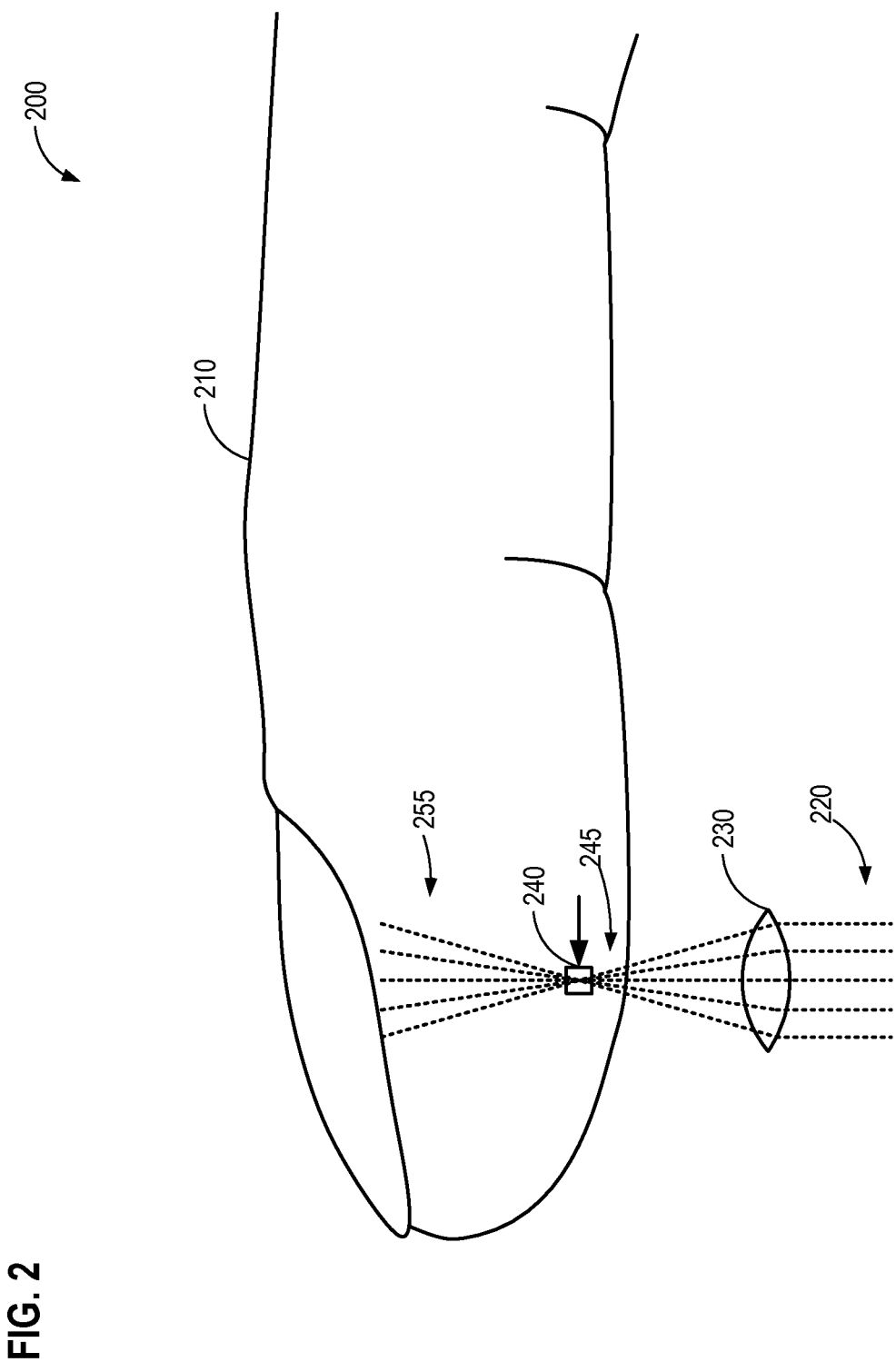
FIG. 2 illustrates a simplified embodiment of a system for delivering electromagnetic radiation onto a finger of a user, according to certain embodiments.

FIG. 2 illustrates a simplified embodiment of a system 200 for delivering electromagnetic radiation 220 focused 245 on a finger 210 of a user. As illustrated, a wide beam of electromagnetic radiation 220 is focused by a lens 230 such that the focused electromagnetic radiation converges at or below the epidermal surface of the user's finger 210. Only at the focus point 240, is the radiation fluence sufficiently high to stimulate, directly or indirectly, an action potential within the finger 210. The electromagnetic radiation may diverge 255 and/or be absorbed/scattered after stimulating the action potential within the finger 210.

According to various embodiments, units of energy may be expressed in terms of fluence or Joules per square centimeter. In various embodiments, the electromagnetic radiation 220 used to excite the action potential may be between 1 $mJ/cm^2$ and 100 $J/cm^2$. For example, the energy of individual pulses may be between approximately 0.1 and 25 $J/cm^2$. Outside of the focus point 240, the fluence may be sub-threshold for action potential initiation and of lower fluence, resulting in less tissue heating. In some embodiments, an actuator may mechanically rotate, move, vibrate, and/or otherwise direct the electromagnetic radiation 220. In another embodiment, the electromagnetic radiation 220 and/or the lens 230 may rotate, move and/or vibrate using beam steering capabilities due to mirrors, spatial light modulators, or other optical and/or electrical methods. The actuator may control the procession of the electromagnetic beam to mitigate collateral tissue heating.

Figure 3:
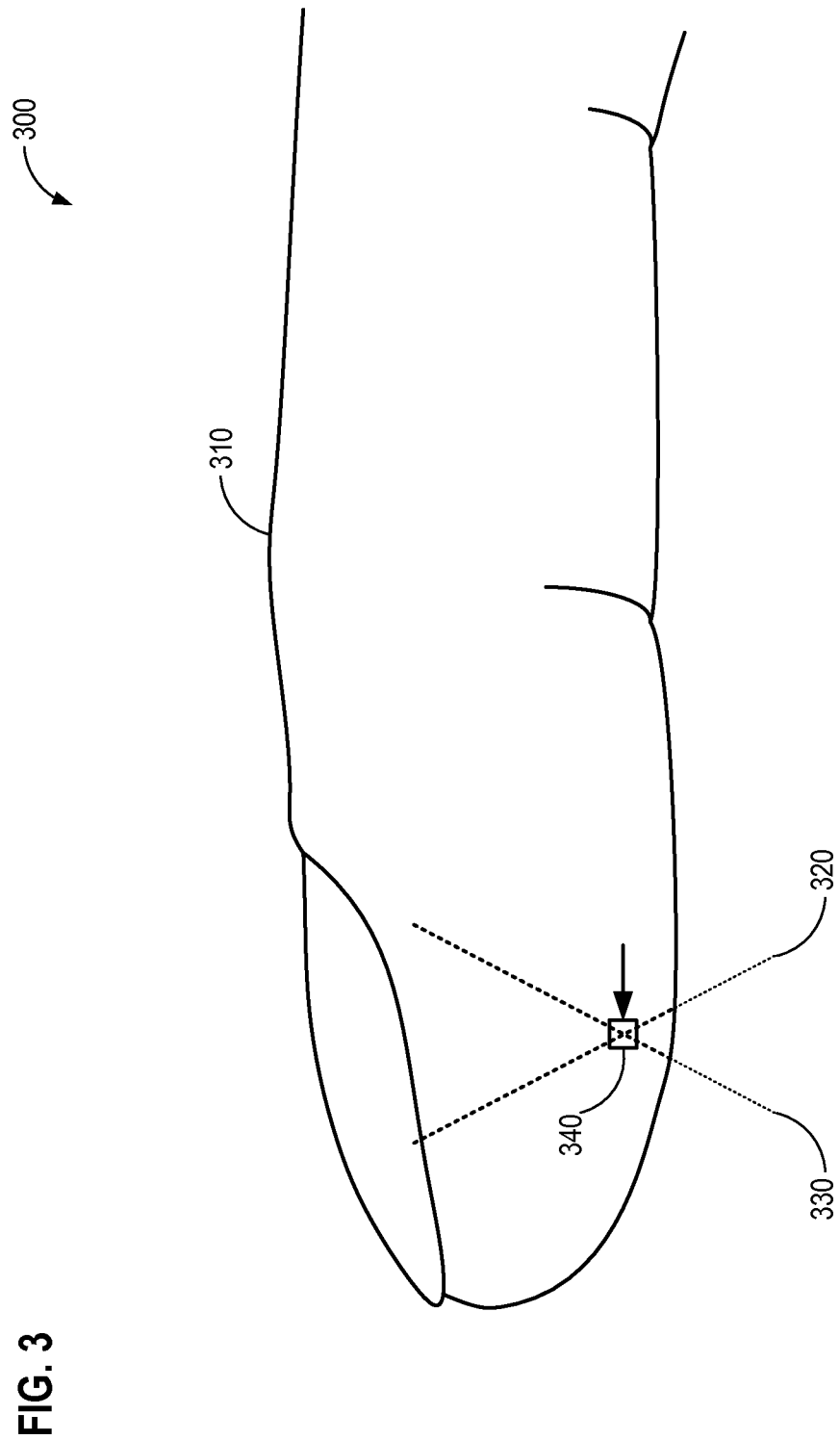
FIG. 3 illustrates a simplified embodiment of multiple electromagnetic radiation beams transcutaneously coincident within a finger of a user, according to certain embodiments.

FIG. 3 illustrates a simplified embodiment of a system 300 for delivering multiple electromagnetic radiation beams 320 and 330 transcutaneously coincident, at 340, on a finger of a user. Two beams 320 and 330 are shown in the illustrated embodiment, but any number of beams may be used. Each of the beams 320 and 330 may have insufficient energy densities to excite tissue and, thus minimize the energy imparted to non-excitable tissue. The point of coincidence 340 may include the combined energy densities of each of the beams 320 and 330 of electromagnetic radiation. Thus, at the point of coincidence 340, the energy density may be sufficient to initiate an action potential. In some embodiments, the size of the focus may be adapted to create different sensory effects. In some embodiments, the size of the focal spot may also be dynamically adjusted.

Figure 4:
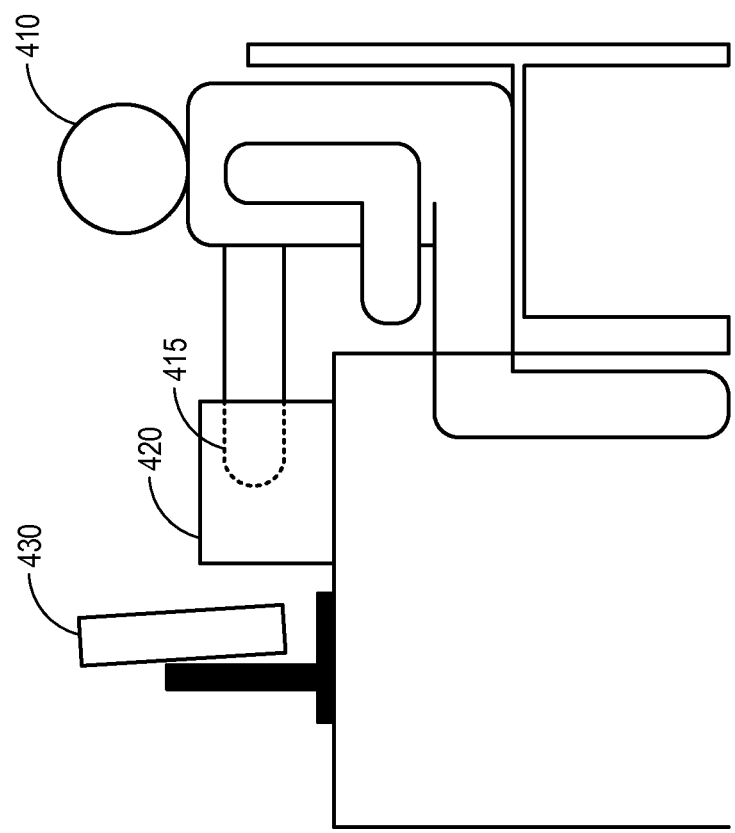
FIG. 4 illustrates a display associated with a system for inducing cutaneous sensations via transcutaneously focused electromagnetic radiation, according to certain embodiments.

FIG. 4 illustrates a display 430 associated with a system 420 for inducing haptic sensations via transcutaneously focused electromagnetic radiation. In various embodiments, the system 420 may be in communication with the display 430. Accordingly, a portion 415 of the user 410 within the system 420 may receive cutaneous sensations induced by transcutaneously focused electromagnetic radiation. As illustrated, the system 420 may be a hand enclosure configured to receive a hand of a user. In such an embodiment, a user may receive cutaneous sensation associated with images, objects, icons, or the like on the display 430. In some embodiments, the finger or hand of the user may be immobilized. In other embodiments, the finger or hand of the user may move within the system 420 and/or be able to provide responses to the received cutaneous sensations induced by the system 420. The power supply, light source, lensing system, and feedback systems may be all housed in the single enclosure. According to other embodiments, various components may be housed in multiple enclosures. Further, a user's finger or hand could be suspended at a distance above a stimulating surface rather than coming into direct contact with a stimulating surface.

Figure 5A:
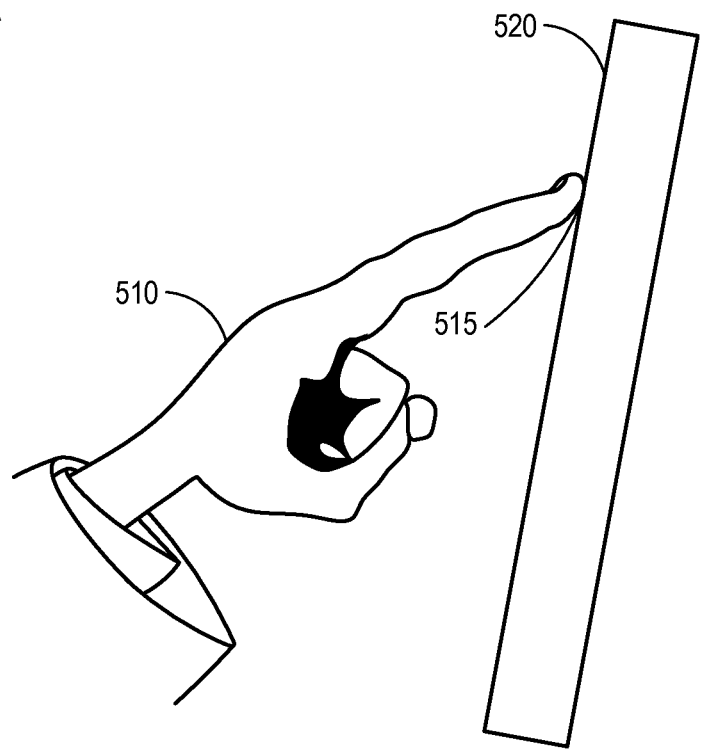
FIG. 5A illustrates a touch screen configured to induce cutaneous sensations in a user's finger by delivering electromagnetic radiation to a point of contact with the user, according to certain embodiments.

FIG. 5A illustrates a display screen 520 configured with a system to induce cutaneous sensations in a user's finger 515 using transcutaneously delivered electromagnetic radiation. The illustrated embodiment is an example of an on-display configuration. Display 520 could be part of a mobile device, such as a smartphone or tablet computer, a stationary device such as a desktop computer, interactive public display, industrial control station, surgical control station, and/or other interactive display device. In the illustrated embodiment, the finger 515 of a user 510 comes into contact with the display 520, upon which the image is displayed. In some embodiments, the optical energy may be delivered through the front of the display.

In one embodiment, a system for inducing cutaneous sensations via transcutaneously focused electromagnetic radiation may be in the form of a flat surface adjacent to or opposite a display surface. For example, on a mobile phone or a tablet computer, the system could be integrated into a flat surface that is beside, beneath, and/or on the sides of a display surface. Such an embodiment may allow for tactile interaction with the content displayed without obscuring any portion of the visual display. A light source according to any of the various embodiments described herein may utilize various types of lasers, VCSELs, LEDs, and/or other high-density focusable light sources.

Figure 5B:
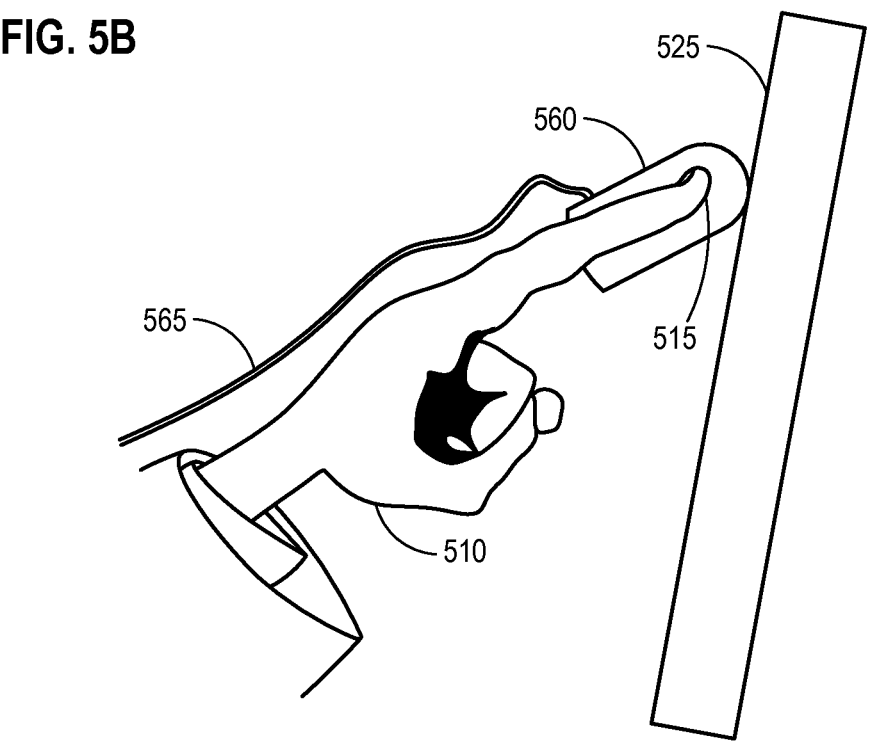
FIG. 5B illustrates an accessory component configured to induce cutaneous sensations in a user's finger while using a display by delivering electromagnetic radiation to a point of contact between the accessory and the user, according to certain embodiments.

FIG. 5B illustrates an accessory component 560 configured to induce cutaneous sensations in a user's finger 515 via transcutaneously focused electromagnetic radiation while using a display 525. In the illustrated embodiment, the electromagnetic radiation may be transmitted through the accessory device 560 (illustrated as a finger sleeve) into the finger 515 of the user 510. The electromagnetic radiation may originate from a remote source and be transmitted via a fiber optic cable 565 to the accessory component 560. In some embodiments, the accessory component 560 may secure the finger 515 suspended away from the walls thereof to avoid mechanical stimulation due to physical contact with external objects, such as the display 525.

Optical components for focusing the electromagnetic radiation and/or feedback sensors and components may be incorporated into the accessory component 560. In some embodiments, an interaction mechanism between the external wall of the accessory component 560 and the display 525 may allow the user to interact with the virtual or distant object shown on the display 525 and experience the tactile sensations in a natural manner. For example, the interaction mechanism may utilize a laser distance finder, capacitive touch screen, an image sensor, a camera, a 3D or depth camera, and/or an ultrasound echolocation system.

Figure 5C:
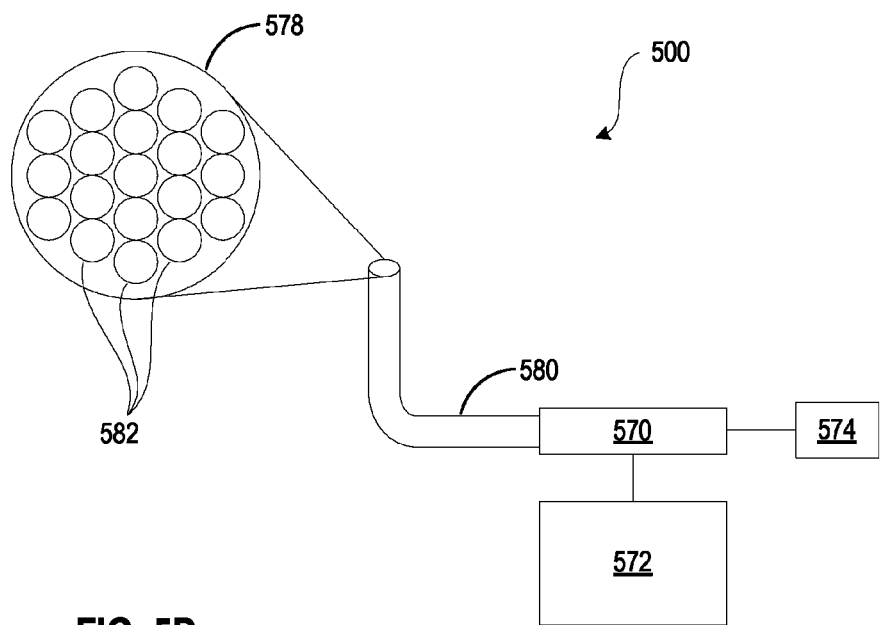
FIG. 5C illustrates a conceptual representation of an electromagnetic radiation delivery system including a single electromagnetic radiation source that may be incorporated into a finger sleeve or other device, according to certain embodiments.

FIG. 5C illustrates a conceptual representation of an electromagnetic radiation delivery system 500 including a single electromagnetic radiation source 574 that may be incorporated into a finger sleeve or other device, according to certain embodiments. System 500 may include a switch controller 572 coupled to an optical switch 570. Electromagnetic radiation source 574 may be coupled to optical switch 570. A plurality of fiber optic cables 582 may be bundled in a cable 580.

An enlarged view of a distal end 578 of cable 580 shows the plurality of fiber optic cables 582. Optical switch 570 may selectively direct electromagnetic radiation generated from electromagnetic radiation source 574 to any one of the plurality of fiber optic cables 582.

Figure 5D:
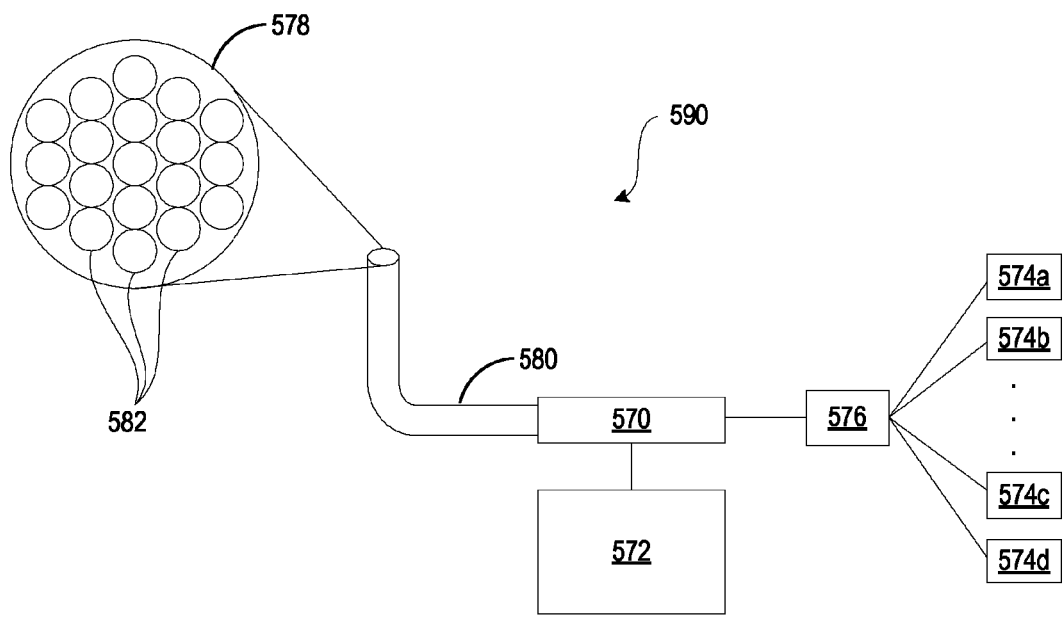
FIG. 5D illustrates a conceptual representation of an electromagnetic radiation delivery system 580 including a plurality of electromagnetic radiation sources that may be incorporated into a finger sleeve or other device, according to certain embodiments.

FIG. 5D illustrates a conceptual representation of an electromagnetic radiation delivery system 590 including a plurality of electromagnetic radiation sources 574a-574d that may be incorporated into a finger sleeve or other device, according to certain embodiments. System 590 may include a number of components that are similar to system 500, and accordingly, similar reference numbers are utilized. System 590 also includes a fiber combiner 576. System 590 may utilize a plurality of electromagnetic radiation sources 574a-574d in order to realize an increase in power output, a decrease in the cost of the system or other potential advantages.

Figure 6B:
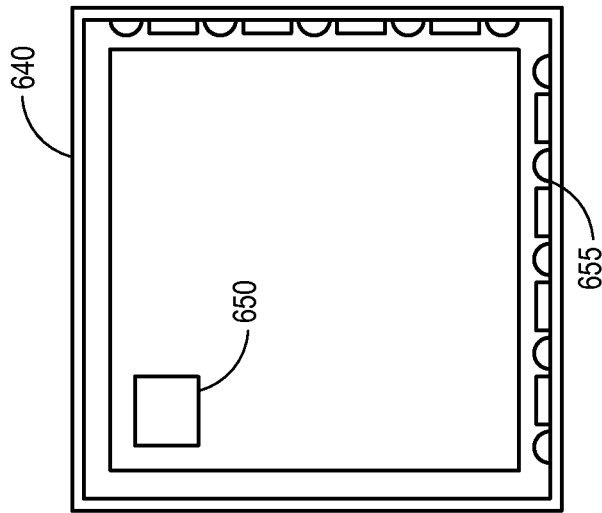
FIG. 6B illustrates another embodiment of a moveable stage for transcutaneously rastering electromagnetic radiation to excite tissue, according to certain embodiments.
Figure 6A:
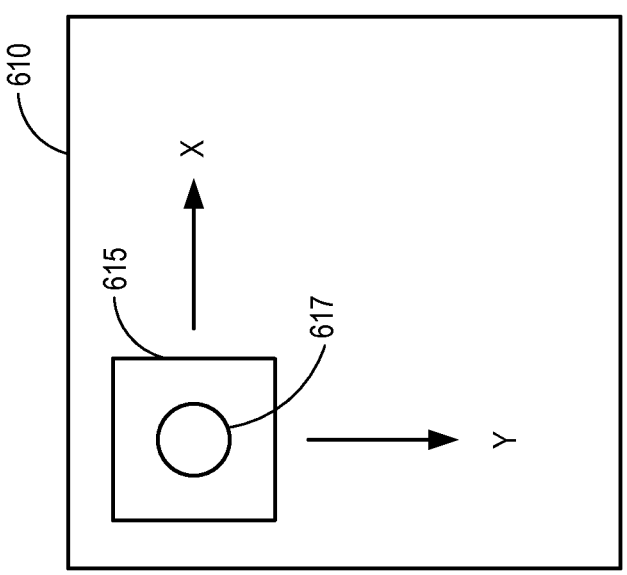
FIG. 6A illustrates an embodiment of a moveable stage for transcutaneously rastering electromagnetic radiation to excite tissue, according to certain embodiments.

FIG. 6A illustrates an embodiment of a stage 615 with a moveable electromagnetic radiation source 617 for rastering electromagnetic radiation to transcutaneously excite tissue. A system, according to any of the various embodiments described herein, may utilize a moveable electromagnetic radiation source 617 to control where the electromagnetic radiation is transcutaneously focused. In some embodiments the stage 615 contains the electromagnetic radiation source 617 and optics, while in others it includes only the optics or only the electromagnetic radiation source 617. In some embodiments, the stage 615 may be behind a display 610 (or other user interface component such as a track pad or dedicated haptic feedback surface), while in other embodiments the stage 615 may be in front of the display 610. In the latter embodiment, the stage 615 may be substantially transparent to visible light, such that the display 610 is not or minimally impeded. The mechanism for moving the stage 615 may be mechanically and/or electromagnetically controlled.

For example, as illustrated in FIG. 6B, the stage 650 may contain lightweight permanent magnets that would be attracted to or repelled from certain areas by a grid or array of controllable electromagnets 655. These electromagnets 655 can reside either on the rear of the display 640 or along a frame around the display 640, so as to not occlude the display 640 for the user. In an embodiment where the electromagnetic radiation source is not incorporated into the stage 650 itself, the source 660 may be in the same plane as the stage, but off to the side of the field. The electromagnetic radiation may be directed from the source to the stage 650 where it is reflected and/or refracted by optical components and focused into the intended tissue.

The ability to raster the electromagnetic radiation beam may be useful for stimulating multiple points when simulating mechanical stimuli. Any of a wide variety of rasterizing systems, methods, and patterns may be used. For example, a galvanometer based scanner or beam splitter with shuttering technologies may be utilized. Microelectromechanical system (MEMS) based reflection and direction of the beam may be used to rasterize the beam. In one embodiment, the tip of one or more laser fibers with external optical lens(es) (i.e., separate from the delivery fibers) may be attached to the stage 650. The laser fiber and external optics may be collectively called the laser head. The plan of the assembly and stage 650 may be parallel to the plane on which a finger, fingers, hand, or other portion of the body is to be stimulated. The stage 650 may be moveable in order to reach all areas of the finger or full hand.

Figure 7C:
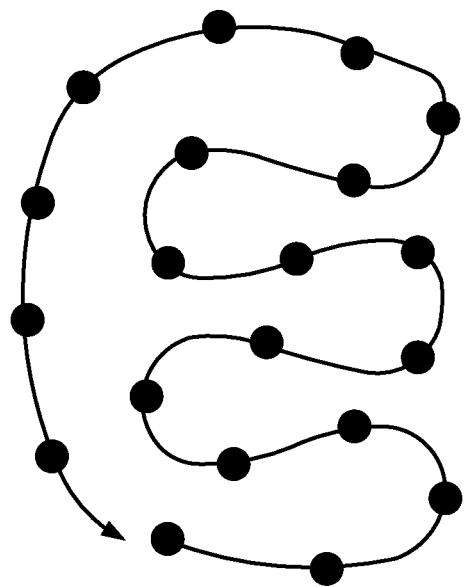
FIGS. 7A-C illustrate examples of rasterization patterns for inducing cutaneous sensations using electromagnetic radiation, according to certain embodiments.
Figure 7B:
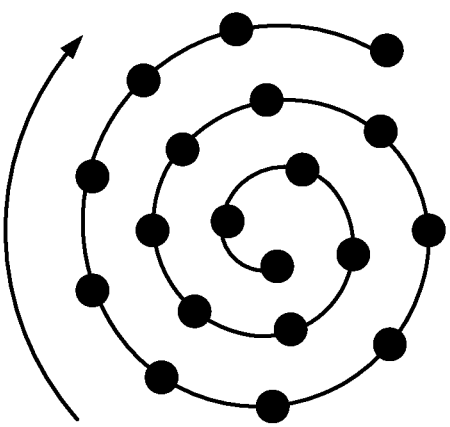
Figure 7A:
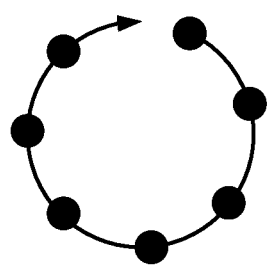

A controller may move the stage 650 based position information in the x-y direction. The position of the stage 650 may be determined by encoders or position sensors 665 on each axis of the stage 650 and/or near the edges of the display 640. The controller may also periodically move the beam, such that the procession irradiates a certain location on the finger pad/hand for only a certain amount of time. The procession of the beam can be in multiple patterns, all contained within the area smaller than two-point discrimination, as described above. FIGS. 7A-7C illustrate three example procession patterns that may be used within a two-point discrimination region to reduce thermal buildup on the tissue. FIGS. 7A-7C may also be examples of rasterization patterns used to induce various cutaneous sensations at desired locations. In such embodiments, the various points in the patterns illustrated in FIGS. 7A-7C may be separated by more than two-point discrimination.

In some embodiments, the same tissue location may be irradiated repeatedly using different light source parameters, such as, but not limited to, pulse widths, frequencies, energies and/or waveforms for each pulse or series of pulses. The control system may track the energies and exposure time delivered to each spot on the tissue and adjust the pulses based on the feedback data to induce the appropriate sensations and avoid injury. If the tissue is moved relative to the light source, there may be a need to increase the power delivered to the previously unexposed tissues. Tracking tissue placement relative to the area of irradiation may allow the control program to deliver the appropriate power to the tissue to induce the desired sensation.

Figure 8:
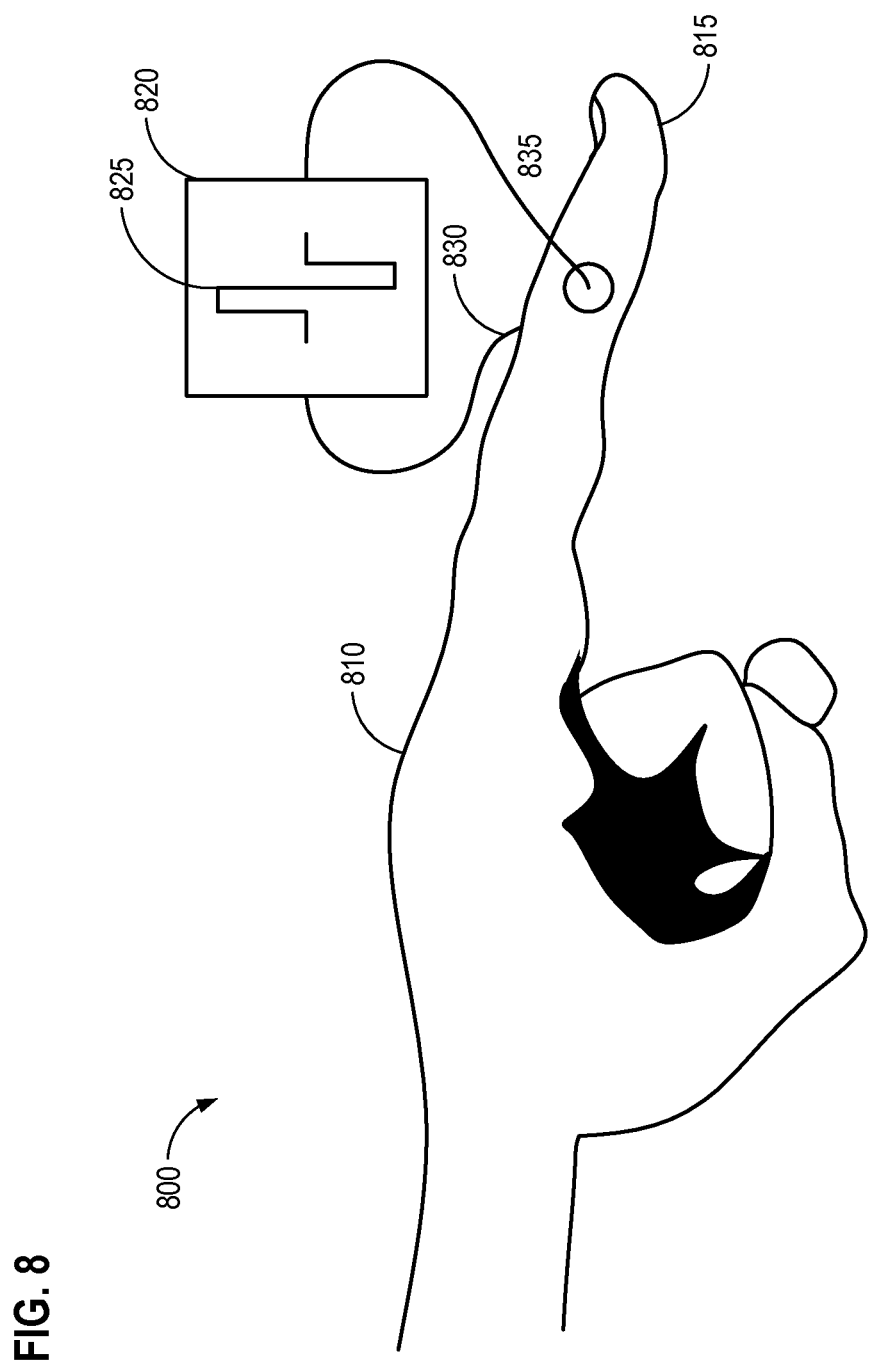
FIG. 8 illustrates an electro-optical system for inducing cutaneous sensations, including an electrical stimulation system and a system for transcutaneously focusing electromagnetic radiation, according to certain embodiments.

FIG. 8 illustrates an electro-optical system 800 for inducing cutaneous sensations, including an electrical sub-threshold-inducing device 820 and a system for transcutaneously focusing electromagnetic radiation according to any of the various embodiments described herein (not shown). As illustrated, electrodes 830 and 835 leading from an electrical stimulator 820 may be attached to a finger 815 of user 810. The electrodes 830 and 835 may be attached away from the area to be optically stimulated to avoid mechanical stimulation. The sub-threshold electrical stimulation may utilize any of a wide variety of waveform shapes, such as square 825, or another waveform, such as sinusoidal, triangular, trapezoidal, monopolar, and/or bipolar. The electrical stimulation may be sub-threshold for all or most sensory modalities. It may be used to reduce the activation threshold necessary to induce cutaneous sensations using transcutaneously focused electromagnetic radiation. If the transmembrane potential of the mechanoreceptor, its afferent axon, or other excitable cells are raised closer to the action potential threshold, then less electromagnetic radiation may be required to directly or indirectly initiate the action potential.

Figure 9:
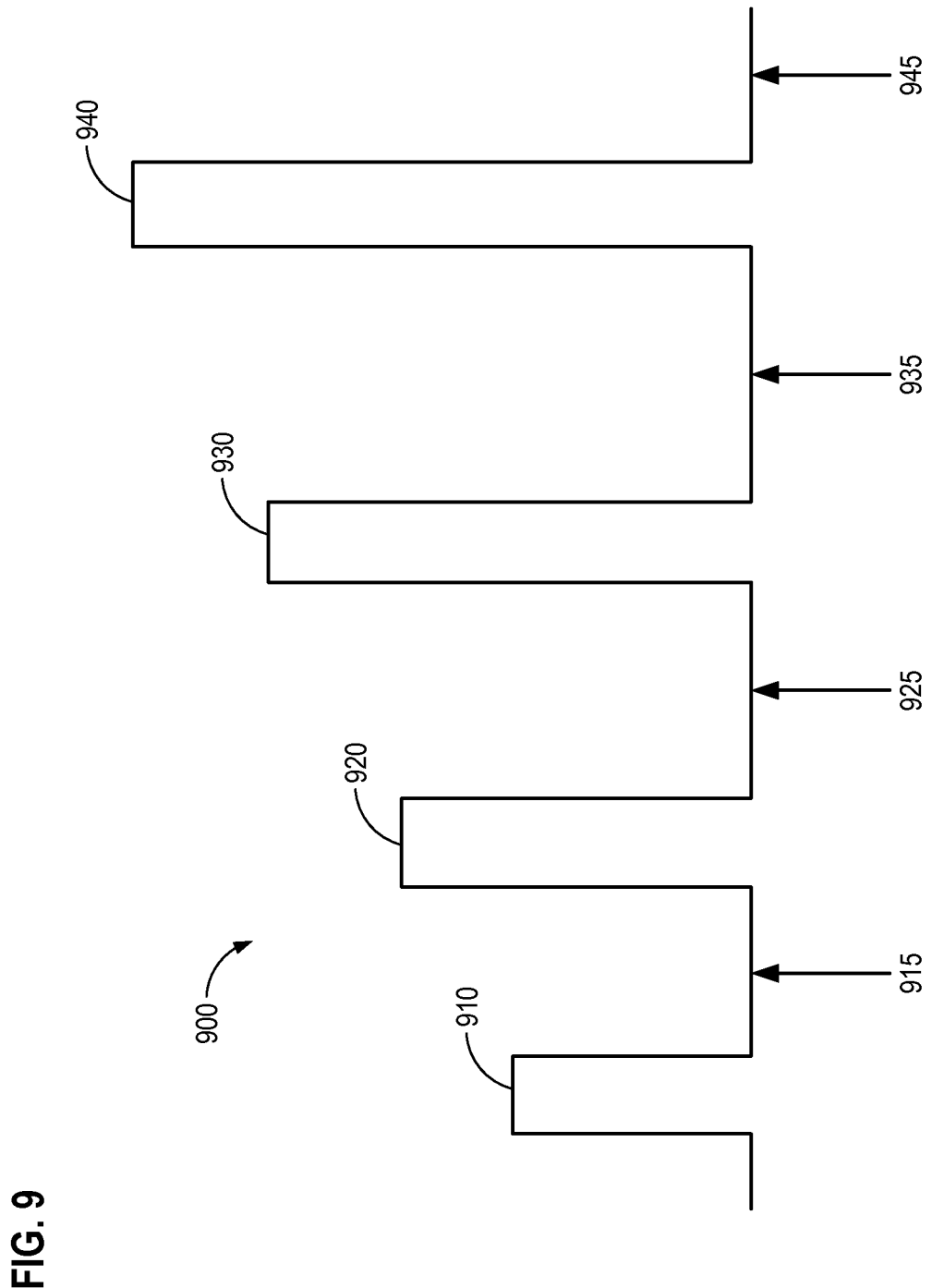
FIG. 9 illustrates a schematic of an initial user calibration procedure of a device including an electromagnetic radiation stimulation system for inducing cutaneous sensations.

FIG. 9 illustrates a schematic 900 of a user calibration procedure, according to one embodiment. The energies required to transcutaneously induce a cutaneous sensation using electromagnetic radiation may differ for each user. For example, the pigmentation and other intrinsic characteristics, such as the finger print pattern or skin optical properties, of each user's skin can be different. Accordingly, in some embodiments a controller may perform an initial calibration for each user and/or use.

A calibration procedure may include imparting energies that should initially be sub-threshold, followed by successively higher energy levels. The user may respond by indicating to the control program whether or not a sensation was felt. FIG. 9 illustrates progressively higher energy levels as peaks 910, 920, 930, and 940, followed by troughs 915, 925, 935, and 945, respectively. In some embodiments, the control program may deliver the next, higher energy stimuli only after receiving some response or after a time period has past during which a response would have been expected. A calibration procedure may also be used to determine the range of fluences that may be used (e.g., the lowest energy that can be felt and the highest energy density that won't cause harm or be uncomfortable). The calibration procedure may be used for various cutaneous sensations, such as tactile and temperature/heating sensations.

According to some embodiments, a calibration procedure may be based on continuously delivering groups of pulses that step up to higher energy levels after predetermined periods of time. Each group of pulses may include a priming pulse that proceeds a train of identical pulses. The priming pulse may reduce sensation latency at the new energy level.

Part of the calibration procedure may account for feedback variables, such as skin temperature, skin tone, incident pressure on stimulation surface, finger speed, and duration of previous exposure. In some instances, when using multiple fingers it is possible that different fingers would have different calibration results. In such cases, the program or controller may keep track of the fingers individually, delivering the appropriate energies to each finger (or other region of the body).

Figure 10:
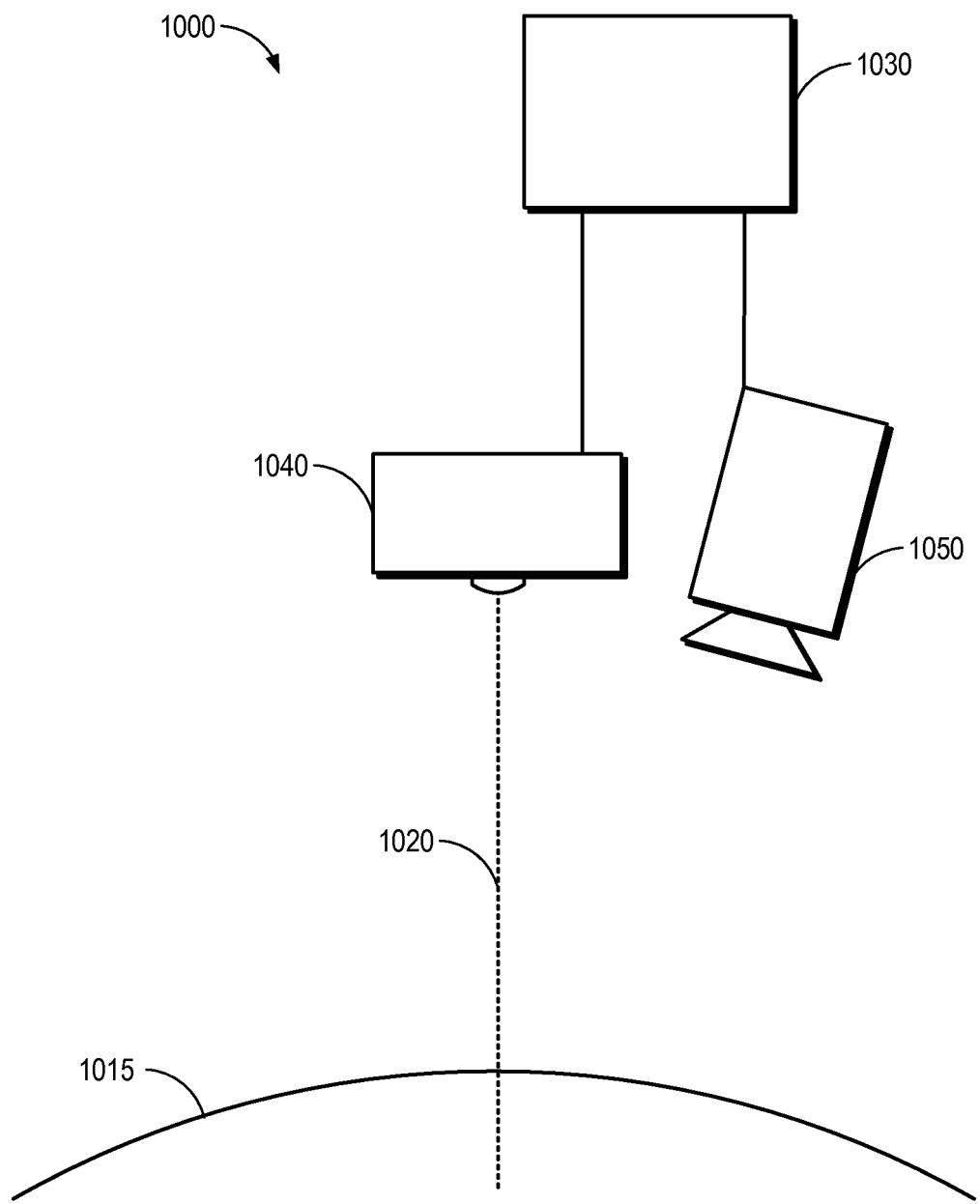
FIG. 10 illustrates a block diagram of a system for inducing cutaneous sensations using electromagnetic radiation including a thermal feedback system, according to certain embodiments.

FIG. 10 illustrates a block diagram of a system 1000 for inducing cutaneous sensations via transcutaneously focused electromagnetic radiation, including a thermal feedback system 1050. As illustrated, an electromagnetic radiation source and/or optics 1040 may impart energy via a beam 1020 to tissue 1015. The energy may be the stimulus for direct or indirect excitation of mechanoreceptors and/or neural or other excitable tissue. Output from the electromagnetic radiation source may be adjusted based on tissue temperature to deliver the appropriate energy to create sensation. At certain wavelengths the byproduct of the light beam incident on the tissues may be thermal energy buildup (heat). A thermal feedback system 1050 may measure the radiation from the tissues to determine the temperature of the tissues. If the tissues become too hot, then the controller 1030 may lower the intensity of the light beam output by the system.

Any type of temperature sensor or detector, such as a thermistor, may be used to determine the temperature of the finger. The feedback system 1050 may be in physical contact with the tissue 1015. In another embodiment, the thermal feedback system 1050 may be a non-contact sensor. A sensor may be placed to the periphery of the surface so as to not distort or impede the passage of the stimulating light. Sensors may be integrated into the surface or display and/or made from materials transparent to the necessary wavelengths of stimulating light and, in the case of a visible display, visible light. As with the thermal imager above, the temperature data may feed the algorithm(s) that adjust the stimulation output appropriately.

The temperature of the stimulating surface may be controlled. For example, in an embodiment where the tissue is in contact with a surface through which stimulation passes. Such an embodiment may not have a temperature feedback system. The surface temperature could be actively heated (or cooled) through any number of mechanisms including, but not limited to, embedded electric heating filaments, thermoelectric heat pump, IR radiation, or directing the heat from other processes such as the computer or graphics processor.

Figure 11:
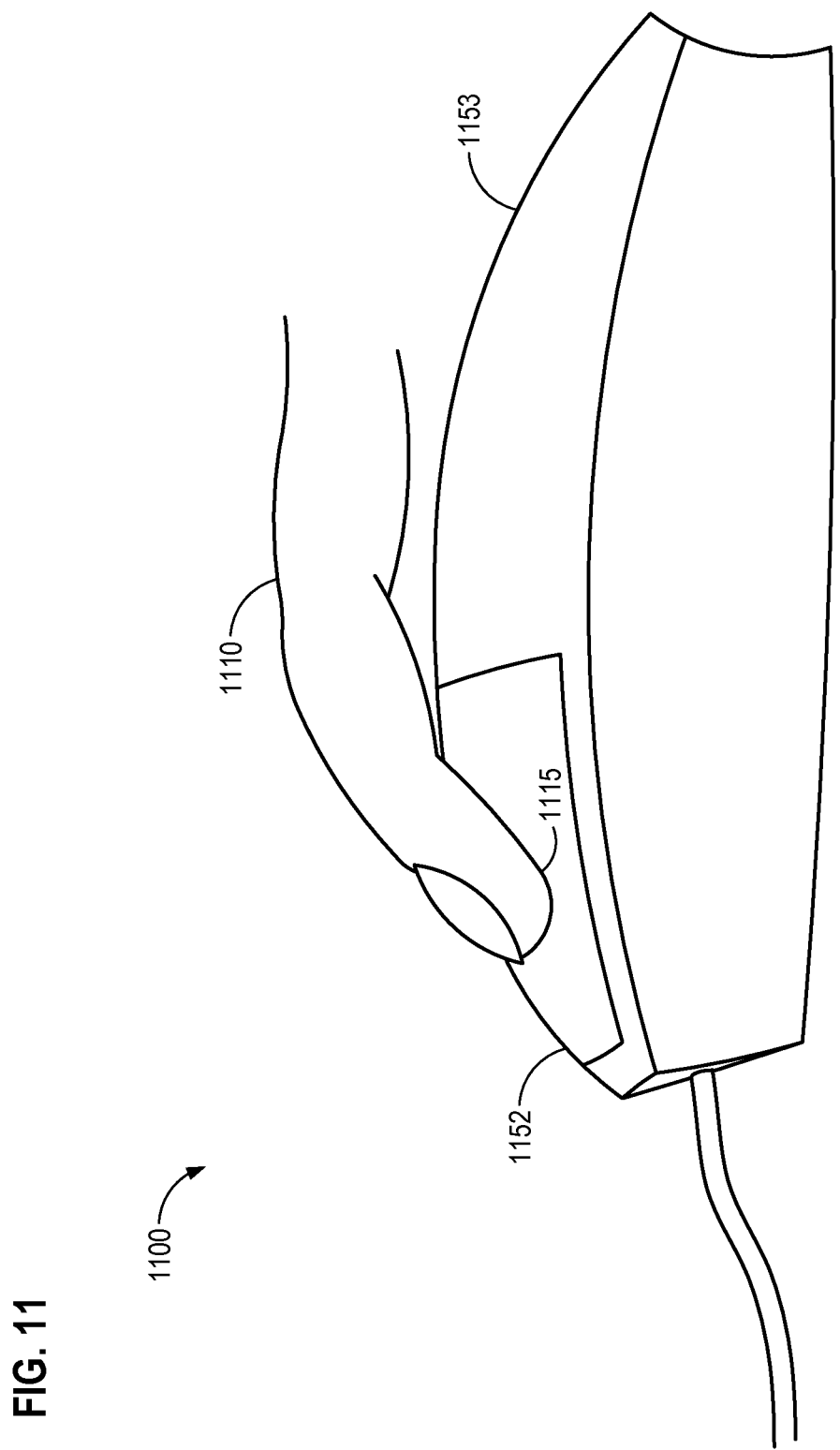
FIG. 11 illustrates a system integrated within a peripheral device of a computer for inducing cutaneous sensations using electromagnetic radiation, according to certain embodiments.

FIG. 11 illustrates a system 1100 for transcutaneously inducing cutaneous sensations integrated within a peripheral device 1153 of a computer. A sensation-inducing system according to any of the various embodiments described herein may be incorporated into any of a wide variety of peripheral control devices, such as the illustrated computer mouse 1153. The finger 1110 used to control the mouse 1153 may have a finger pad 1115 on a control surface 1152. A system configured to induce cutaneous sensations using transcutaneously focused electromagnetic radiation may be integrated with the control surface 1152. A pressure sensitive feedback mechanism may be used to modulate the imparted stimulation in proportion to the pressure exerted by the user. In another embodiment, the finger pad 1115 may be held away from any physical surface similar to the concept described in conjunction with FIG. 5B.

Figure 12A:
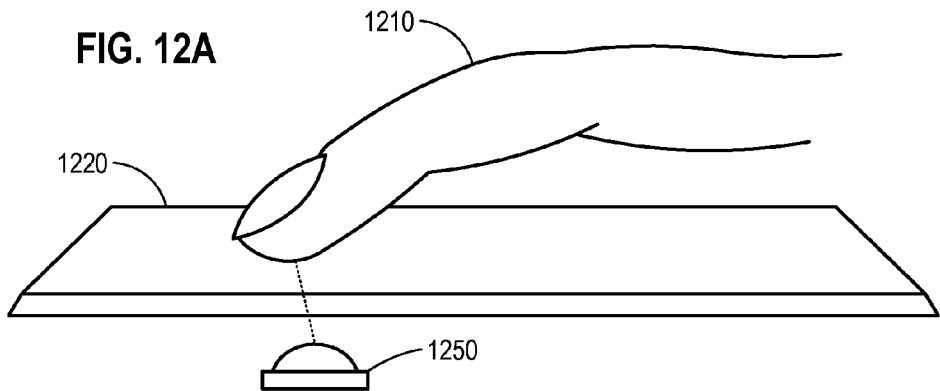
FIGS. 12A-C illustrate three embodiments for directing electromagnetic radiation to a point of contact using electromagnetic radiation within a surface, according to certain embodiments.
Figure 12B:
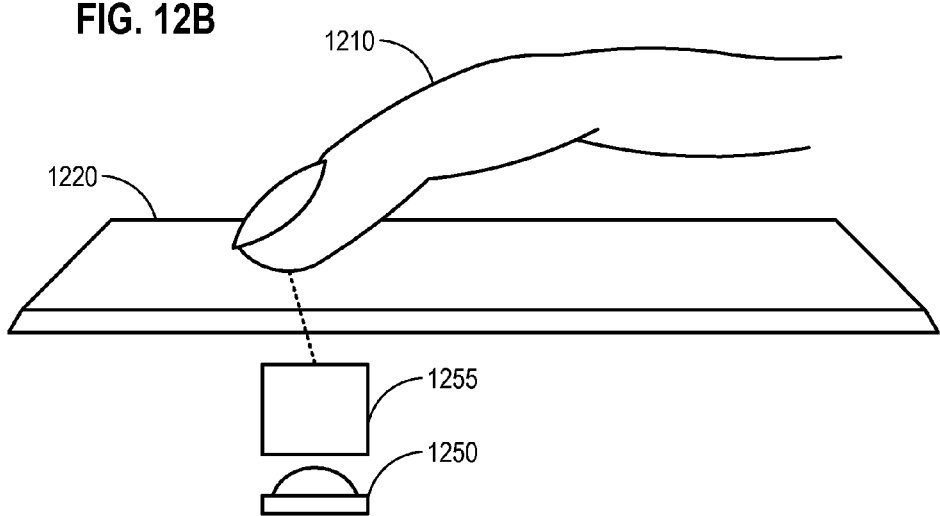
Figure 12C:
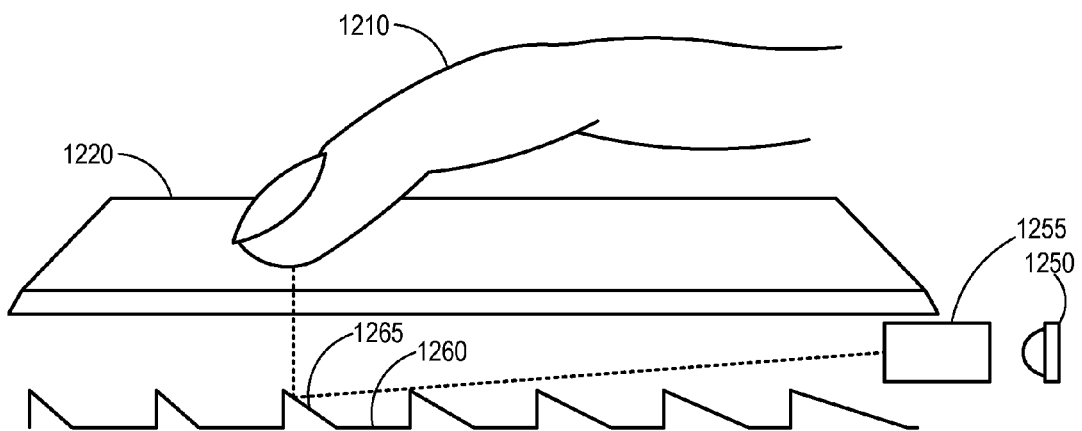

FIGS. 12A-C illustrates three embodiments for incorporating a system for inducing cutaneous sensations via transcutaneously focused electromagnetic radiation within a surface 1220. As illustrated in FIG. 12A an electromagnetic radiation source 1250 may be positioned beneath a surface 1220, such as a touch pad, track pad, or display. For example, the surface 1220 may be part of an off-display embodiment where there is no visual information conveyed, or it could be a visible display that is interactive both for vision and touch. In an embodiment in which the surface 1220 is a display, the display could be any number of different display types including, but not limited to, LCD, LED, OLED, AMOLED, e-ink, array of controllable mirrors, or digital micromirror device. The display may be substantially transparent to the electromagnetic radiation used for stimulation.

Alternatively, the electromagnetic radiation from the source 1250 may be transmitted via channels or vias in the surface 1220. FIG. 12A illustrates an embodiment in which a source 1250 is directly beneath the surface 1220. FIG. 12B illustrates an embodiment in which electromagnetic radiation from the source 1250 is directed by an optical scanner 1255 through the surface 1220 and onto/into a finger 1210. FIG. 12C illustrates an embodiment in which electromagnetic radiation from a source 1250 is directed through an optical scanner 1255 to a series of reflective mirrors 1260 with angled surfaces 1265 in order to reflect the electromagnetic radiation onto/into the finger 1210 of a user. The optical scanner 1255 may be configured to irradiate multiple points on the finger to induce cutaneous sensations.

Figure 13:
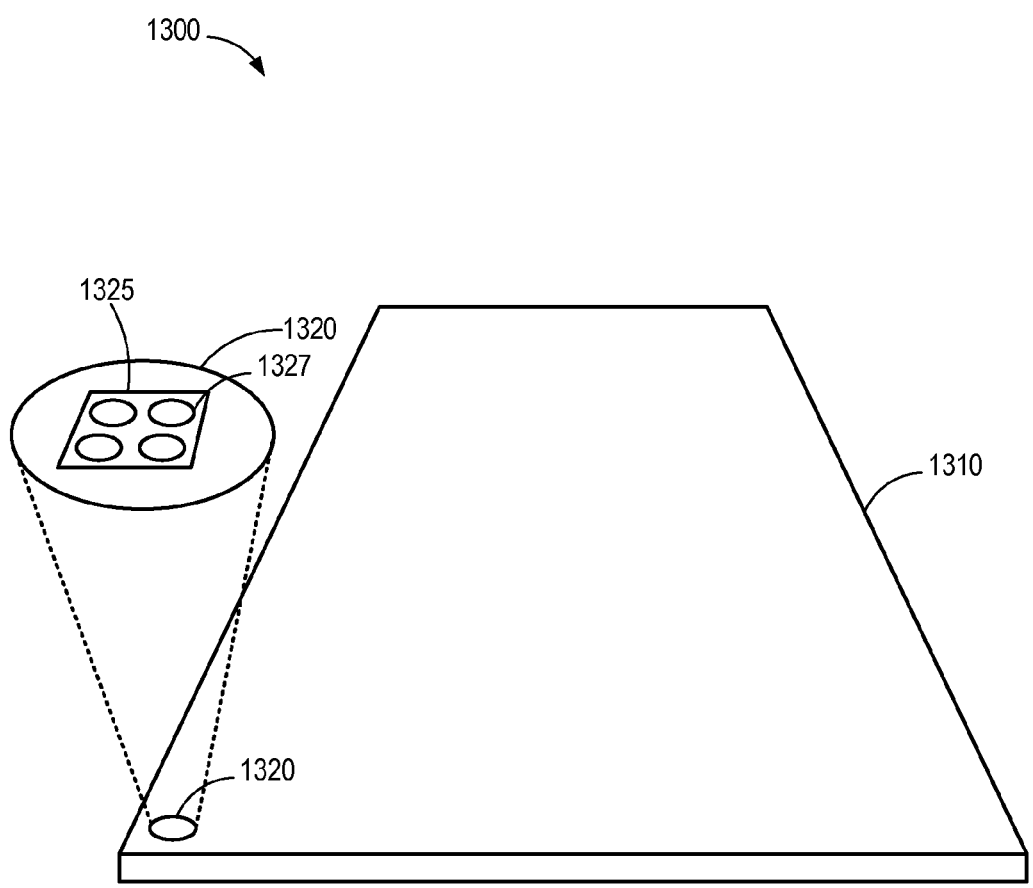
FIG. 13 illustrates an example of a display incorporating a system for inducing cutaneous sensations using electromagnetic radiation, according to certain embodiments.

FIG. 13 illustrates an example of a display 1300 with an integrated system 1320 for inducing cutaneous sensations via transcutaneously focused electromagnetic radiation. As illustrated, a display surface 1310 may include a series of LEDs or other visible light sources 1327 clustered on the display as pixels 1325. Electromagnetic radiation sources for inducing cutaneous sensations via transcutaneously focused electromagnetic radiation may be integrated within the display surface. In some embodiments, the electromagnetic radiation sources may be formed on the same substrate. The electromagnetic radiation sources may include LEDs, laser diodes, IR light sources, VSCELs, and/or other suitable sources. The proximity of the sensation inducing sources to the finger of a user may reduce the power requirements required to induce sensations. A digitizer or other technology may be used to sense the location and area of contact of a user's finger (or fingers, hand, portion of the body, etc.). Limiting stimulating emissions to those areas where the target tissue is touching the screen may minimize energy waste.

Figure 14A:
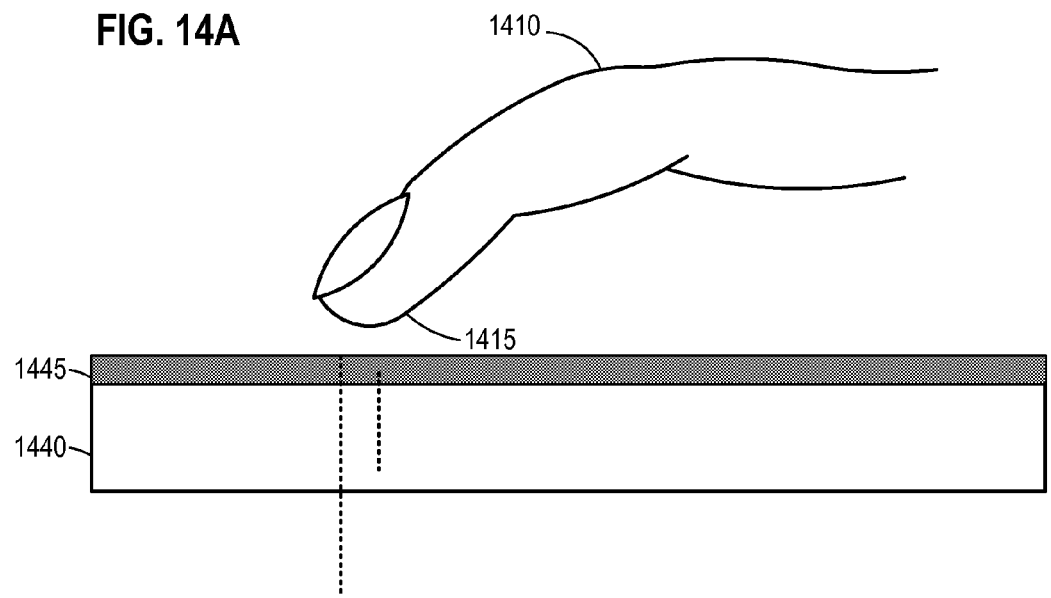
FIG. 14A illustrates a schematic of a relatively thin fluid layer configured to provide ocular protection from electromagnetic radiation that may be used to induce haptic sensations, according to certain embodiments.
Figure 14B:
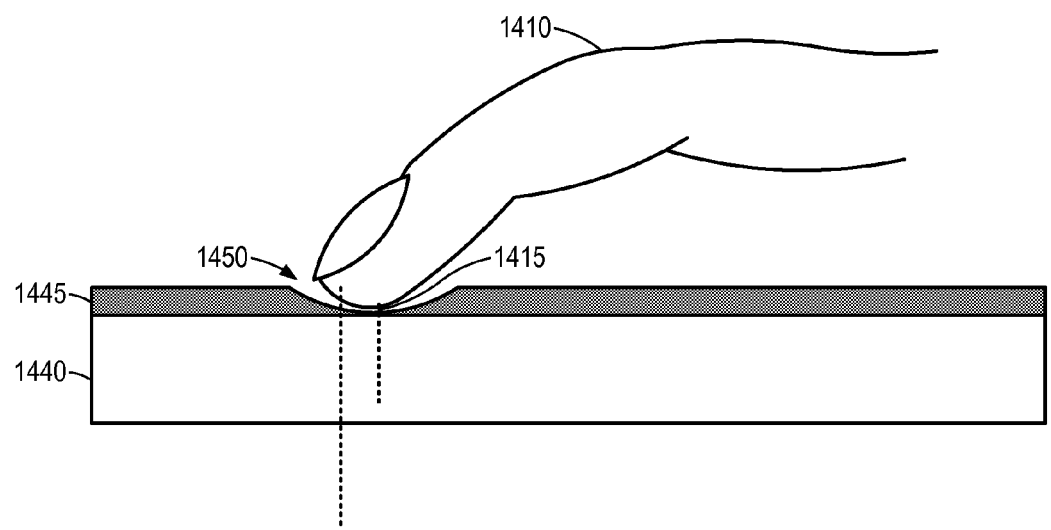
FIG. 14B illustrates a finger depressing the relatively thin fluid layer, thereby allowing electromagnetic radiation to penetrate the fluid layer and induce a cutaneous sensation in the finger of the user, according to certain embodiments.

It may be desirable to minimize or eliminate sensation-inducing electromagnetic radiation in any location except for a desired location and area of contact (i.e., where a finger is). Certain wavelengths of electromagnetic radiation may cause damage to the eye at high intensities, such as the corneal surface, lens, or retina. FIG. 14A illustrates a schematic of a relatively thin fluid layer 1445 on a surface 1440 configured to prevent stray electromagnetic radiation emissions. The fluid layer 1445 may absorb, reflect, or refract sensation-inducing electromagnetic radiation and prevent it from negatively impacting a user. FIG. 14B illustrates a finger 1410 depressing the relatively thin fluid layer 1445 with a finger pad 1415. The depression 1450 may vacate a sufficient amount of the fluid to allow the sensation-inducing electromagnetic radiation to penetrate the finger pad 1415. The fluid layer 1445 may allow visible light to pass with minimal attenuation and optical distortion.

Figure 15A:
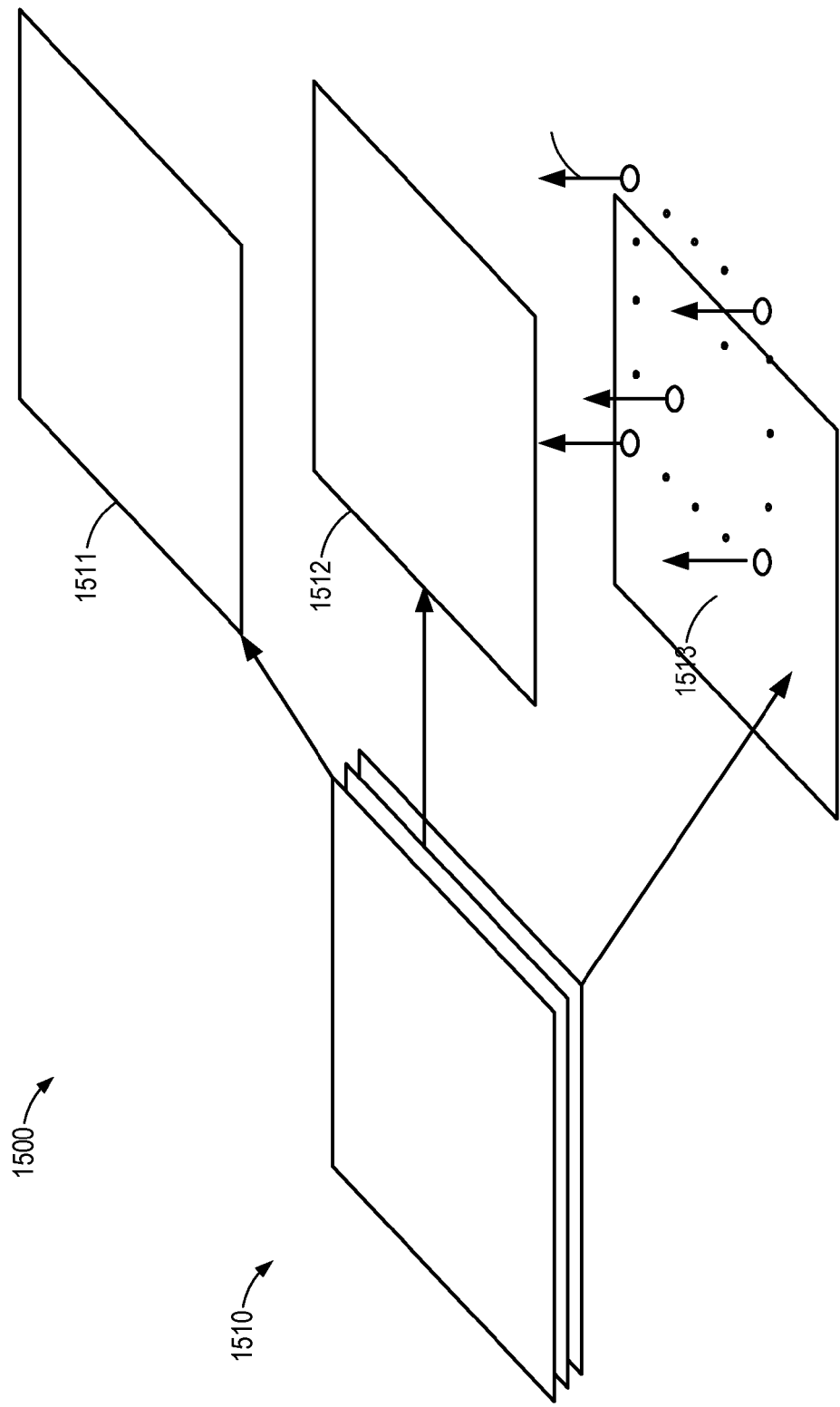
FIG. 15A illustrates an embodiment of a display incorporating a system for inducing cutaneous sensations using electromagnetic radiation and an array of lenslets and/or VCSELs, according to certain embodiments.
Figure 15B:
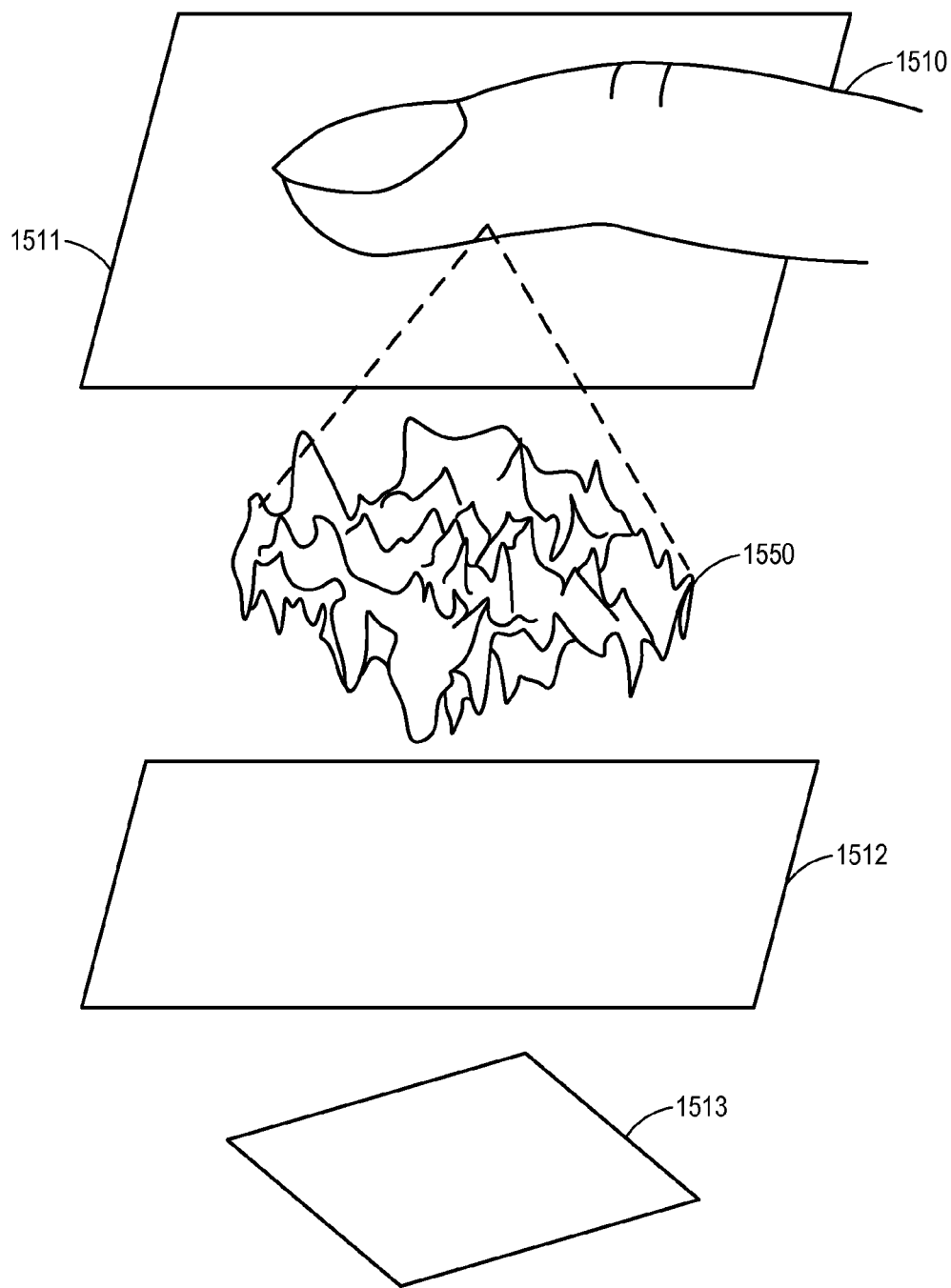
FIG. 15B illustrates an embodiment of a display, in which collimated electromagnetic radiation traverses a transmissive spatial light modulator layer.
Figure 15C:
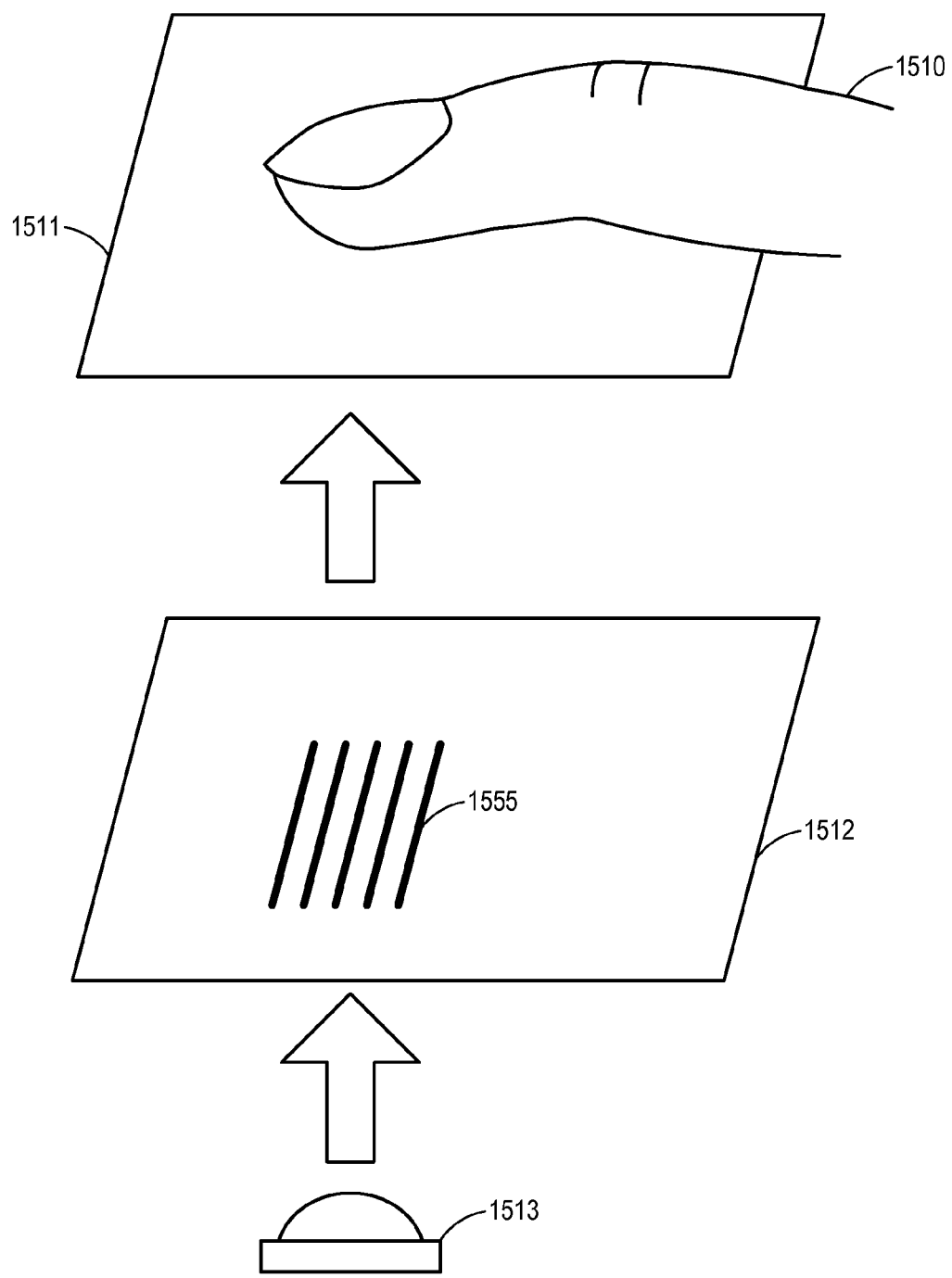
FIG. 15C illustrates an embodiment of a display including a spatial light modulating layer, which may impose a grating or dot pattern for scanning stimulation spots and rasterization schemas.

FIGS. 15A-15C illustrate an embodiment of a display 1510 with an integrated system for inducing cutaneous sensations via transcutaneously focused electromagnetic radiation, utilizing an array of lenslets and VCSELs 1513. As illustrated in FIG. 15A, a touch screen display 1510 may include one or more functional layers 1511, 1512, and 1513 manufactured as a single physical layer or as discrete physical layers. A touch sensitive layer 1511 may be configured to receive touch inputs from a finger or fingers of a user. A transmissive or reflective Spatial Light Modulator (SLM) Layer 1512 may be configured to modulate visible light and/or other electromagnetic radiation. A third layer 1513 may include an N×N array of lenslets with integrated VCSELs. Each lenslet may be a discrete lens aligned with a VCSEL in order to collimate the upward emitting VCSEL output.

As illustrated in FIG. 15B, the collimated electromagnetic radiation may then traverse the transmissive spatial light modulator layer 1512 where the wavefront 1550 could be arbitrarily modulated prior to being transmitted through the touch sensitive layer 1511. The electromagnetic radiation from the VCSELs may be used to induce cutaneous sensations by transcutaneously focusing the electromagnetic radiation on a user's finger(s) 1510. In various embodiments, the electromagnetic radiation may be transmitted through the display/touch screen layer(s) 1511. For instance, if the wavelength of the sensation-inducing electromagnetic radiation is about 1300 nm, the electromagnetic radiation may be transmitted with minimal loss through silicon. Furthermore, in various embodiments, the location of the finger 1510 on the touch screen 1511 may be detected by the touch screen and used by the controller of the system for inducing cutaneous sensations via transcutaneously focused electromagnetic radiation.

In various embodiments, the SLM layer 1512 may be used to optimize focusing on the surface or inside human tissue through close-loop feedback control. For example, the wavefront of the electromagnetic radiation may be modulated in a systematic fashion. After each alteration of the wavefront, a user may provide feedback based on the strength of the tactile sensation. Convergence to an optimum wavefront may be achievable after a number of iterations during an initial calibration phase. An adaptive focusing scheme may be used to increase focal intensity by several folds. The focused/modulated electromagnetic radiation may be scanned over the finger by imposing a dynamically changing phase grating pattern using the SLM layer 1512. SLM based optical scanning has the advantage of size and speed, eliminating the need for mechanical scanner and the inertia associated with it.

Additionally, as illustrated in FIG. 15C, the SLM layer 1512, may impose a grating or dot pattern 1555 for scanning stimulation spots and rasterization schemas. The grating 1555 may be formed as a distinct layer in addition to the SLM layer 1512, or in place of the SLM layer 1512. Additionally, it may be possible to create a variety of static patterns using diffractive optical elements and/or selectively activating pixels of the SLM.

The above description provides numerous specific details for a thorough understanding of the embodiments described herein. However, those of skill in the art will recognize that one or more of the specific details may be omitted, modified, and/or replaced by a similar process or system.

What is claimed is:

1. A system for inducing a cutaneous sensation in association with an electronic display, comprising:
    an electromagnetic radiation emission system configured to emit electromagnetic radiation in an infrared spectrum, the electromagnetic radiation suitable to excite neural tissue;
    an electronic display configured to display graphical information to the user;
    a detection system configured to detect a point of contact of at least one finger with the electronic display; and
    a controller configured to transmit a control signal to the electromagnetic radiation emission system to cause the electromagnetic radiation emission system to deliver electromagnetic radiation at the point of contact of the finger detected by the detection system, the electromagnetic radiation suitable to excite neural tissue in order to induce a sensation.

2. The system of claim 1, wherein the electromagnetic radiation emission system further comprises at least one focusing element configured to selectively focus the electromagnetic radiation emitted by the electromagnetic radiation emission system.

3. The system of claim 1, further comprising a storage medium containing a library of sensations, each sensation defined by at least one characteristic of electromagnetic radiation, and
wherein the controller is configured to modulate the electromagnetic radiation emitted by the electromagnetic radiation emission system based upon the at least one characteristic to induce at least one of the sensations from the library.

4. The system of claim 3, wherein the sensation corresponds to an object displayed on the electronic display at the point of contact of the finger.

5. The system of claim 1, wherein the electromagnetic radiation emission system comprises a laser.

6. The system of claim 1, wherein the electronic display is a touch screen electronic display, and
wherein the detection system utilizes a touch screen digitizer of the touch screen electronic display to detect the point of contact and determine a location of the point of contact.

7. The system of claim 1, wherein the system further comprises:
a thermal feedback system configured to measure a temperature associated with the point of contact, and
wherein the controller is configured to dynamically control the electromagnetic radiation emission system to vary an output energy based on the temperature.

8. The system of claim 1, wherein the induced sensation comprises one of a texture, a shape, a temperature, and a compliance.

9. The system of claim 1, wherein the sensation comprises feedback in response to a user action.

10. The system of claim 9, wherein the user action comprises pressing a button shown on the electronic display.

11. A system for inducing a cutaneous sensation in association with an electronic display, comprising:
an electromagnetic radiation emission system configured to emit electromagnetic radiation in a visible spectrum, the electromagnetic radiation suitable to excite neural tissue;
an electronic display configured to display graphical information to the user;
a detection system configured to detect a point of contact of at least one finger with the electronic display; and
a controller configured to transmit a control signal to the electromagnetic radiation emission system to cause the electromagnetic radiation emission system to deliver electromagnetic radiation at the point of contact of the finger detected by the detection system, the electromagnetic radiation suitable to excite neural tissue in order to induce a sensation.

12. The system of claim 11, wherein the electromagnetic radiation emission system further comprises at least one focusing element configured to selectively focus the electromagnetic radiation emitted by the electromagnetic radiation emission system.

13. The system of claim 11, further comprising a storage medium containing a library of sensations, each sensation defined by at least one characteristic of electromagnetic radiation, and
wherein the controller is configured to modulate the electromagnetic radiation emitted by the electromagnetic radiation emission system based upon the at least one characteristic to induce at least one of the sensations from the library.

14. The system of claim 13, wherein the sensation corresponds to an object displayed on the electronic display at the point of contact of the finger.

15. The system of claim 11, wherein the electromagnetic radiation emission system comprises a laser.

16. The system of claim 11, wherein the electronic display is a touch screen electronic display, and
wherein the detection system utilizes a touch screen digitizer of the touch screen electronic display to detect the point of contact and determine a location of the point of contact.

17. The system of claim 11, wherein the system further comprises:
a thermal feedback system configured to measure a temperature associated with the point of contact, and
wherein the controller is configured to dynamically control the electromagnetic radiation emission system to vary an output energy based on the temperature.

18. A system for inducing a cutaneous sensation in association with a touch screen electronic display, comprising:
a touch screen electronic display configured to display graphical information to a user;
a detection system associated with the touch screen electronic display to detect a point of contact of at least one finger with the touch screen electronic display and determine a location of the point of contact;
a laser emission system configured to emit electromagnetic radiation having a wavelength in one of a visible spectrum and an infrared spectrum, the electromagnetic radiation suitable to transcutaneously excite neural tissue to induce a cutaneous sensation to provide tactile feedback to the user;
a controller configured to transmit a control signal to the laser emission system to cause the laser emission system to deliver electromagnetic radiation at the point of contact detected by the detection system, the electromagnetic radiation suitable to excite neural tissue in order to induce a sensation;
wherein the controller is further configured to modulate the electronic radiation based upon at least one characteristic of an object displayed on the touch screen electronic display at the point of contact of the finger.

* * * * *